(12) United States Patent
Basilion et al.

(10) Patent No.: US 11,708,393 B2
(45) Date of Patent: Jul. 25, 2023

(54) TARGETED NON-INVASIVE IMAGING PROBES OF EGFR EXPRESSING CELLS

(71) Applicant: CASE WESTERN RESERVE UNIVERSITY, Cleveland, OH (US)

(72) Inventors: James P. Basilion, Shaker Heights, OH (US); Richard Agnes, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 252 days.

(21) Appl. No.: 17/224,505

(22) Filed: Apr. 7, 2021

(65) Prior Publication Data

US 2021/0221846 A1    Jul. 22, 2021

Related U.S. Application Data

(63) Continuation of application No. 16/396,265, filed on Apr. 26, 2019, now abandoned, which is a continuation of application No. 13/671,957, filed on Nov. 8, 2012, now abandoned.

(60) Provisional application No. 61/557,025, filed on Nov. 8, 2011.

(51) Int. Cl.
 *C07K 7/08* (2006.01)
 *C07K 7/56* (2006.01)

(52) U.S. Cl.
 CPC . *C07K 7/08* (2013.01); *C07K 7/56* (2013.01)

(58) Field of Classification Search
 CPC ...... C07K 2319/00; C07K 7/08; A61K 47/66; A61P 41/00; A61P 43/00
 See application file for complete search history.

(56) References Cited

U.S. PATENT DOCUMENTS

| | | |
|---|---|---|
| 3,909,093 A | 9/1975 | Lundberg |
| 6,479,470 B1 | 11/2002 | Kozikowski et al. |
| 6,528,499 B1 | 3/2003 | Kozikowski et al. |
| 7,038,078 B2 | 5/2006 | Aldrich et al. |
| 7,381,745 B2 | 6/2008 | Kozikowski et al. |
| 7,408,079 B2 | 8/2008 | Pomper et al. |
| 8,078,264 B2 | 12/2011 | Basilion |
| 8,227,634 B2 | 7/2012 | Pomper et al. |
| 8,609,721 B2 | 12/2013 | Kozikowski et al. |
| 8,778,305 B2 | 7/2014 | Pomper et al. |
| 8,907,058 B2 | 12/2014 | Low et al. |

(Continued)

FOREIGN PATENT DOCUMENTS

| | | |
|---|---|---|
| WO | 2010/0018230 A2 | 2/2010 |
| WO | 2014127365 A1 | 8/2014 |

OTHER PUBLICATIONS

Cheng et al. Highly Efficient Drug Delivery with Gold Nanoparticle Vectors for in Vivo Photodynamic Therapy of Cancer. J. Am. Chem. Soc. 2008, 130, 10643-10647.

(Continued)

*Primary Examiner* — Randall L Beane
(74) *Attorney, Agent, or Firm* — Tarolli, Sundheim, Covell & Tummino, LLP

(57) ABSTRACT

A probe for imaging EGFR expressing cells includes an EGFR targeting moiety, a reporter moiety, and a hydrophilic linker that links the EGFR targeting moiety to the reporter moiety. The hydrophilic linker enhances solubility of the probe in an aqueous media as well as binding affinity of the probe to EGFR expressing cells.

7 Claims, 5 Drawing Sheets

Specification includes a Sequence Listing.

(56) References Cited

U.S. PATENT DOCUMENTS

| | | |
|---|---|---|
| 9,056,841 B2 | 6/2015 | Pomper et al. |
| 9,192,302 B2 | 11/2015 | Basilion |
| 9,193,763 B2 | 11/2015 | Low et al. |
| 9,226,981 B2 | 1/2016 | Pomper et al. |
| 9,271,653 B2 | 3/2016 | Basilion |
| 9,314,538 B2 | 4/2016 | Satpayev et al. |
| 9,371,360 B2 | 6/2016 | Pomper et al. |
| 9,694,091 B2 | 7/2017 | Pomper et al. |
| 9,776,977 B2 | 10/2017 | Pomper et al. |
| 9,861,713 B2 | 1/2018 | Pomper et al. |
| 9,884,132 B2 | 2/2018 | Pomper et al. |
| 9,889,199 B2 | 2/2018 | Basilion et al. |
| 9,925,273 B2 | 3/2018 | Pereira et al. |
| 9,951,324 B2 | 4/2018 | Low et al. |
| 10,011,657 B2 | 7/2018 | Gish et al. |
| 10,029,023 B2 | 7/2018 | Pomper et al. |
| 10,039,845 B2 | 8/2018 | Pomper et al. |
| 10,046,054 B2 | 8/2018 | Low et al. |
| 10,188,754 B2 | 1/2019 | Yang et al. |
| 10,232,058 B2 | 3/2019 | Pomper et al. |
| 10,369,113 B2 | 8/2019 | Chandran et al. |
| 10,406,240 B2 | 9/2019 | Low et al. |
| 10,426,850 B2 | 10/2019 | Yu et al. |
| 10,485,878 B2 | 11/2019 | Low et al. |
| 10,500,292 B2 | 12/2019 | Pomper et al. |
| 10,517,956 B2 | 12/2019 | Low et al. |
| 10,517,957 B2 | 12/2019 | Low et al. |
| 10,557,128 B2 | 2/2020 | Low et al. |
| 10,596,259 B2 | 3/2020 | Savariar et al. |
| 10,624,969 B2 | 4/2020 | Low et al. |
| 10,624,970 B2 | 4/2020 | Low et al. |
| 10,624,971 B2 | 4/2020 | Low et al. |
| 10,646,581 B2 | 5/2020 | Low et al. |
| 10,653,806 B2 | 5/2020 | Pomper et al. |
| 10,660,971 B2 | 5/2020 | Li |
| 10,683,272 B2 | 6/2020 | Ray et al. |
| 10,688,198 B2 | 6/2020 | Ray et al. |
| 10,709,794 B2 | 7/2020 | Basilion et al. |
| 10,717,750 B2 | 7/2020 | Pomper et al. |
| 10,722,593 B2 | 7/2020 | Vining et al. |
| 10,736,974 B2 | 8/2020 | Pomper et al. |
| 10,744,206 B2 | 8/2020 | Li |
| 2006/0222595 A1 | 10/2006 | Mukherjee et al. |
| 2007/0160617 A1 | 7/2007 | Ma et al. |
| 2008/0213377 A1 | 9/2008 | Bhatia et al. |
| 2009/0011004 A1 | 1/2009 | Lutz et al. |
| 2009/0297615 A1 | 12/2009 | Wang et al. |
| 2009/0304803 A1 | 12/2009 | Hasan |
| 2010/0048602 A1* | 2/2010 | Riggs-Sauthier .... A61K 31/402 546/46 |
| 2010/0183504 A1 | 7/2010 | Chen |
| 2010/0026068 A1 | 10/2010 | Zhang et al. |
| 2010/0329983 A1* | 12/2010 | Stewart .............. G01N 33/6872 424/9.34 |
| 2011/0165079 A1 | 7/2011 | Lu et al. |
| 2011/0262347 A1 | 10/2011 | Ruoslahti et al. |
| 2011/0268660 A1 | 11/2011 | Danikas et al. |
| 2012/0282632 A1 | 11/2012 | Chiu et al. |
| 2013/0289520 A1 | 10/2013 | Febvay et al. |
| 2013/0315834 A1 | 11/2013 | Praveen et al. |
| 2014/0220143 A1 | 8/2014 | Dhar et al. |
| 2014/0286969 A1 | 9/2014 | Tschoepe et al. |
| 2015/0056132 A1 | 2/2015 | Dennis et al. |
| 2015/0366968 A1 | 12/2015 | Basilion et al. |
| 2016/0067341 A1 | 3/2016 | Low et al. |
| 2018/0106809 A1 | 4/2018 | Dennis et al. |
| 2019/0010237 A1 | 1/2019 | Reilly et al. |
| 2019/0099431 A1 | 4/2019 | Gish et al. |
| 2019/0111150 A1 | 4/2019 | Singh et al. |
| 2019/0262417 A1 | 8/2019 | Leann et al. |
| 2019/0328898 A1 | 10/2019 | Torgov et al. |
| 2019/0328911 A1 | 10/2019 | Krol et al. |
| 2020/0199245 A1 | 6/2020 | Liu et al. |
| 2020/0276331 A1 | 9/2020 | Coumans |
| 2020/0282072 A1 | 9/2020 | Tschoepe et al. |

OTHER PUBLICATIONS

Choi et al. Mechanism of active targeting in solid tumors with transferrin-containing gold nanoparticles. Proc Natl Acad Sci USA. Jan. 19, 2010;107(3):1235-1240.

Ikuta et al. The effect of molecular structure on the anticancer drug release rate from prodrug nanoparticles. 2015,51, 12835-12838.

Li et al. Identification and characterization of a novel peptide ligand of epidermal growth factor receptor for targeted delivery of therapeutics. The FASEB J. 2005 19(14):1978-1984.

Otsuka et al. PEGylated nanoparticles for biological and pharmaceutical applications. vol. 55, Issue 3, Feb. 24, 2003, pp. 403-419.

Samia et al. Semiconductor Quantum Dots for Photodynamic Therapy. J. Am. Chem. Soc. 2003, 125:15736.

Steichen et al. A review of current nanoparticle and targeting moieties for the delivery of cancer therapeutics. Feb. 14, 2013; 48(3): 416-427.

Vagner et al., Bioorganic & Medicinal Chemistry Letter, vol. 14:211-215 (2004).

Craig et al., Langmuir, vol. 24:10282-10292 (2008) {Year: 2008).

Liu et al. {Spacer length effects on in vitro imaging and surface accessibility of fluorescent inhibitors of prostate specific membrane antigen, Bioorganic & Medicinal Letters, vol. 21 :7013-7016, (Oct. 4, 2011).

Bennike {Development of a Novel Peptide Based Probe for Tumour Imaging, Aalborg University, Thesis {Jun. 2011 ), 92 pages.

Agnes et al.. An Optical Probe for Noninvasive Molecular Imaging of Orthotopic Brain Tumors Overexpressing Epidermal Growth Factor Receptor, Mol Cancer Ther, vol. 11(10): OF1-0F10, (published on line Jul. 17, 2012).

DeJesus, Synthesis of [64Cu]Cu-NOTA-Bn-GE11 for PET Imaging of EGFR-Rich Tumors, Current Radiopharmaceuticals, vol. 5(1):15-18 {Jan. 2012).

Song et al. (Peptide Ligand-mediated liposome distribution and targeting to EGFR expressing tumor in vivo, International Journal of Pharmaceutics, vol. 363:155-161 (pub online Jul. 23, 2008).

U.S. Appl. No. 16/573,570, filed Sep. 17, 2019, U.S. Non-Final Rejection dated Jun. 10, 2022, 24 pgs.

U.S. Appl. No. 16/901,874, filed Jun. 15, 2020, U.S. Non-Final Rejection dated Aug. 18, 2022, 13 pgs.

\* cited by examiner

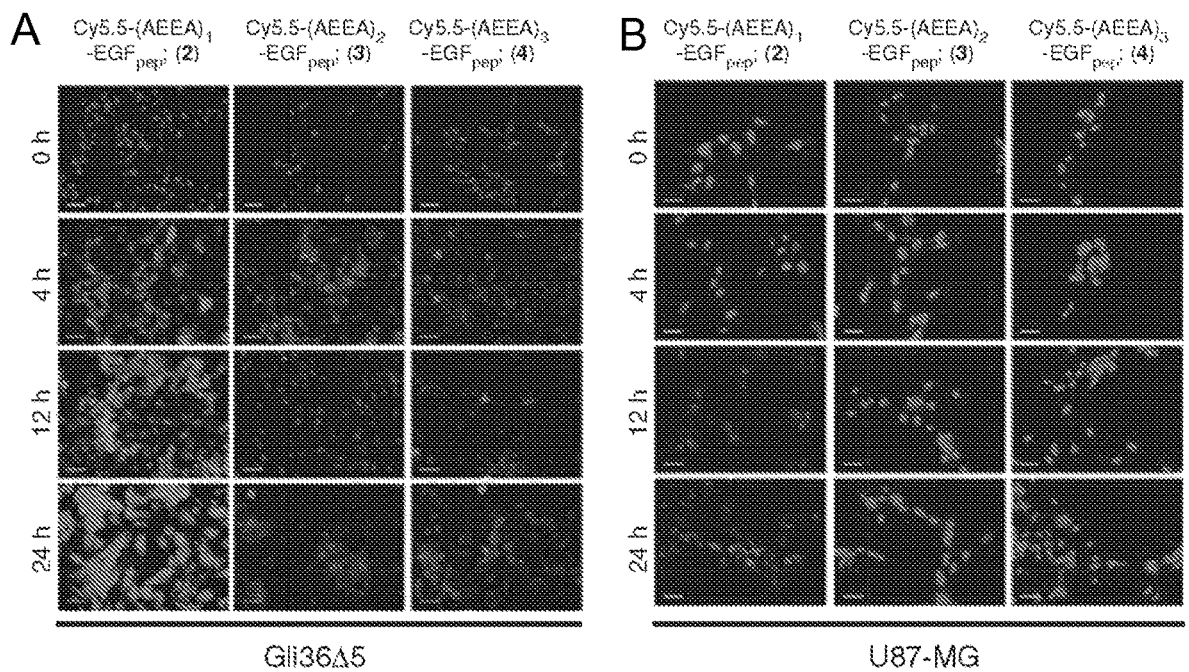
Figs. 3A-B
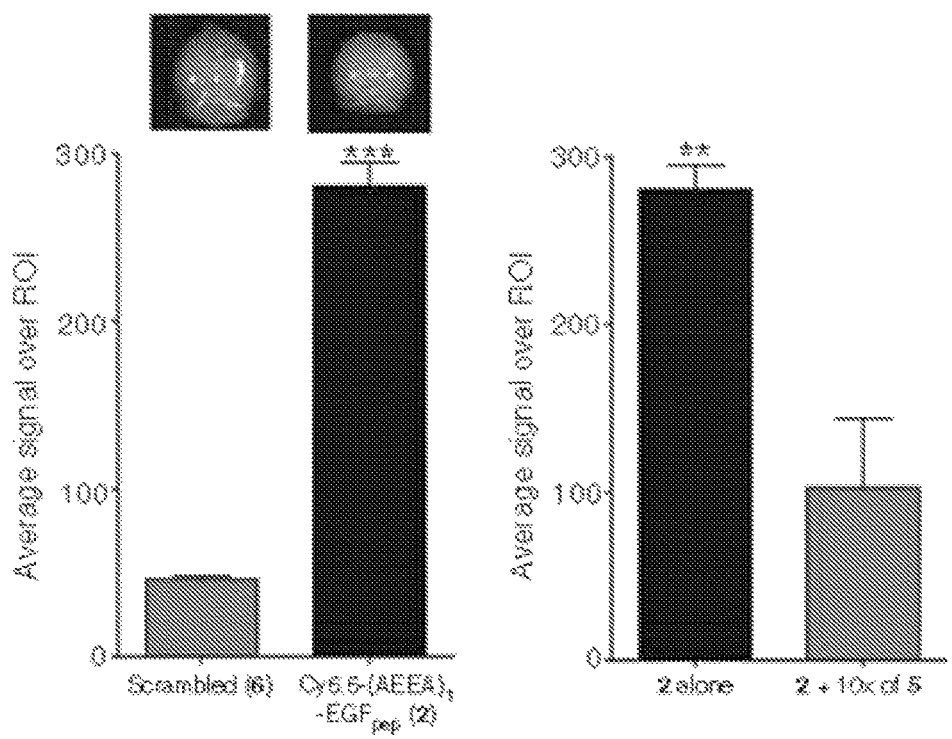
Fig. 4

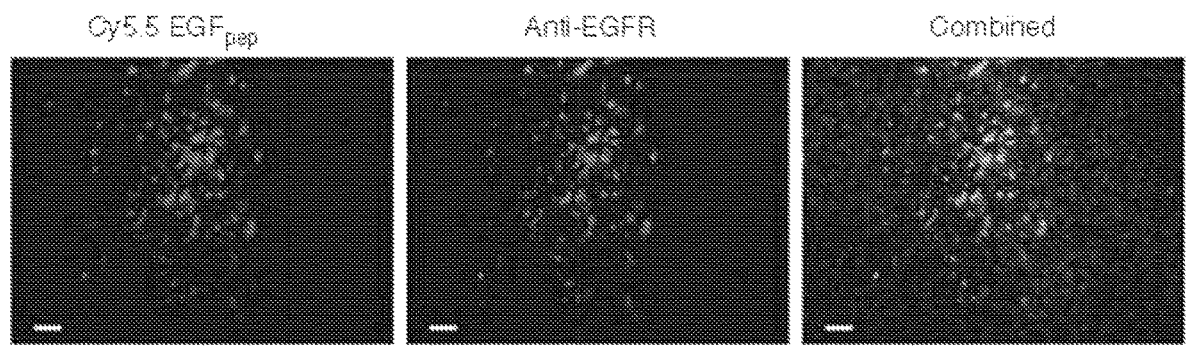
Fig. 5
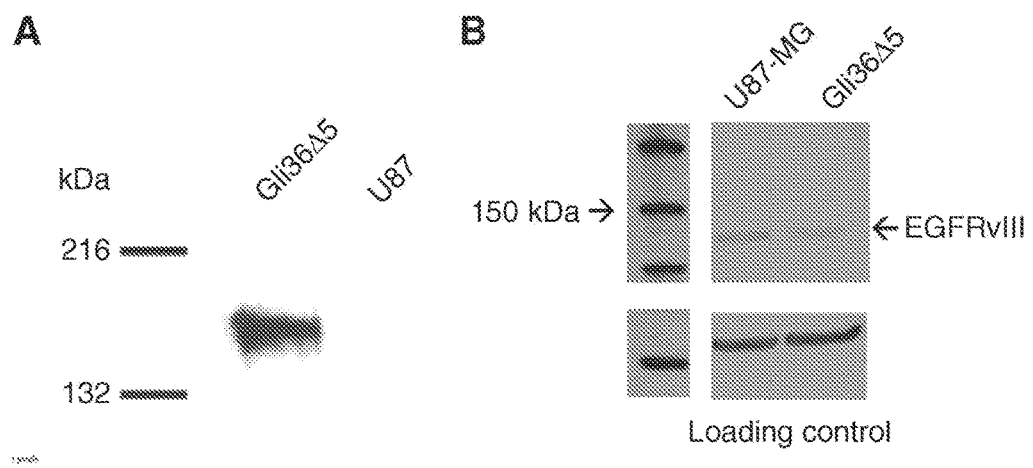
Figs. 6A-B

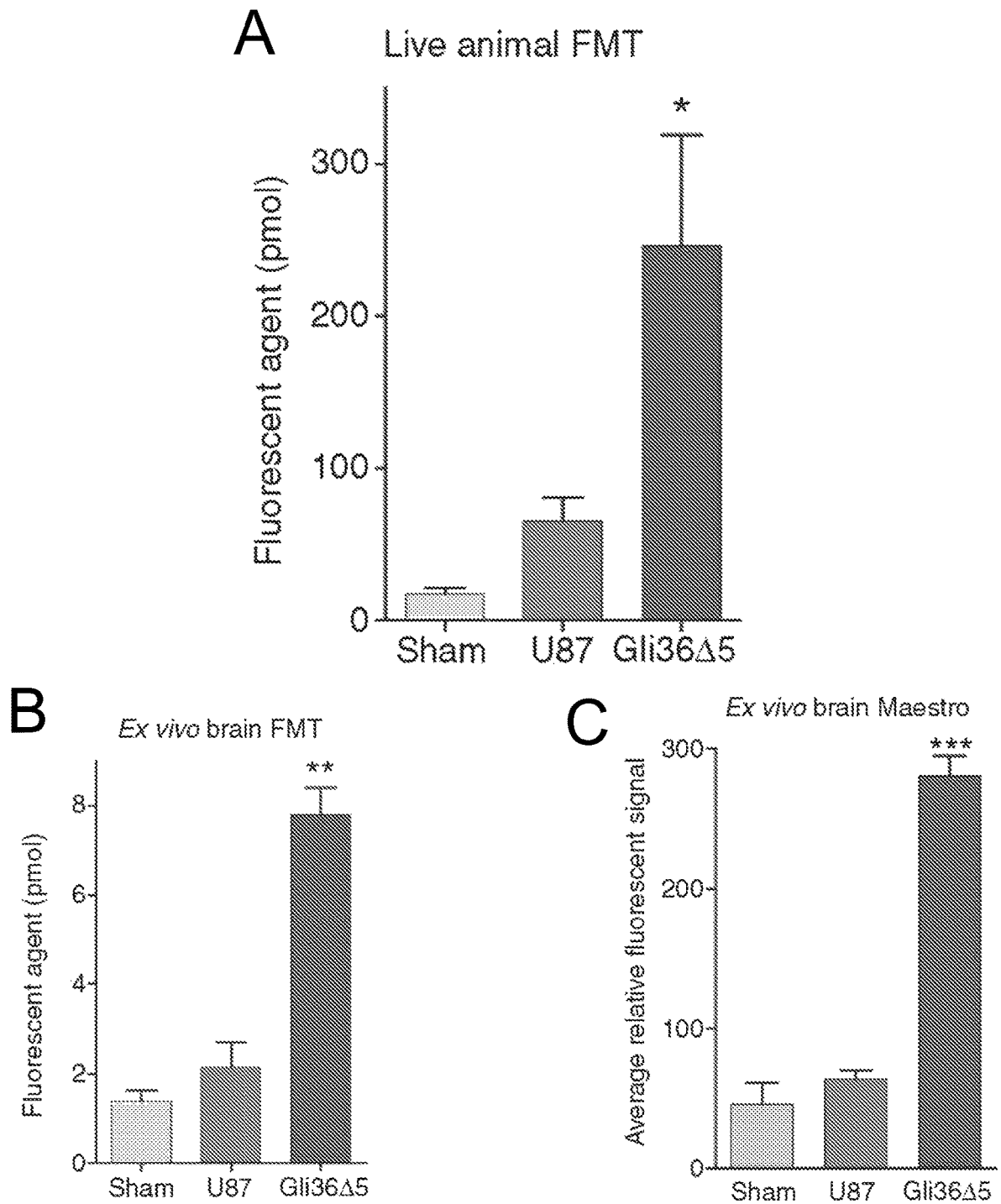
Figs. 8A-C

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Synthetic Construct

<400> SEQUENCE: 1

Tyr His Trp Tyr Gly Tyr Thr Pro Gln Asn Val Ile
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic Construct

<400> SEQUENCE: 2

Tyr His Trp Tyr Lys Tyr Thr Pro Gln Glu Val Ile
1               5                   10
```

TARGETED NON-INVASIVE IMAGING PROBES OF EGFR EXPRESSING CELLS

RELATED APPLICATION

This application claims priority from U.S. Provisional Application No. 61/557,025, filed Nov. 8, 2011, the subject matter of which is incorporated herein by reference in its entirety.

BACKGROUND

Non-invasive optical imaging technologies can be used for diagnosis and monitoring therapeutic response. As optical instrumentation advances (e.g., tomographic imaging), the development of optical imaging agents that are selective for tumors for in vivo or in vitro studies is fast becoming an important field for cancer research. One type of such agents is a molecule labeled with near infrared fluorescence (NIRF) or fluorochrome reporter moiety.

Glioblastoma multiforme (GBM) is the most common and most malignant of the glial tumors. In 40-50% of these tumors, mutations resulting to over expression or activation of epidermal growth factors are found. Epidermal growth factors receptors (EGFR) are cell surface receptors that regulate growth and survival as well as adhesion, migration, differentiation and other cellular processes. The ability to differentially image EGFR expression levels might provide non-invasive means to identify tumor biomarker that can aide in the selection of treatment as well as means of targeted drug delivery.

SUMMARY

This application relates to a probe for imaging EGFR expressing cells of a subject. The probe can include an EGFR targeting moiety, a reporter moiety, and a hydrophilic linker that links or couples the EGFR targeting moiety to the reporter moiety. The hydrophilic linker can enhance solubility of the probe in an aqueous media as well as binding affinity of the probe to EGFR expressing cells.

In some aspects, the EGFR expressing cells can include EGFR expressing cancer cells. The EGFR expressing cancer cells can include glioblastomas as well as solid tumors, such as breast, lung, ovarian, and colon cancers. The probe upon systemic administration to subject is capable of crossing the blood brain barrier, targeting the EGFR expressing cancer cells, and imaging the EGFR expressing cancer cells.

In other aspects, the EGFR targeting moiety can include an EGF peptide ligand having an amino acid sequence of SEQ ID NO: 1 or SEQ ID NO: 2. The reporter moiety can include a fluorochrome, and the linker comprising a polyethylene glycol linker.

In one embodiment, the probe can include the following formula:

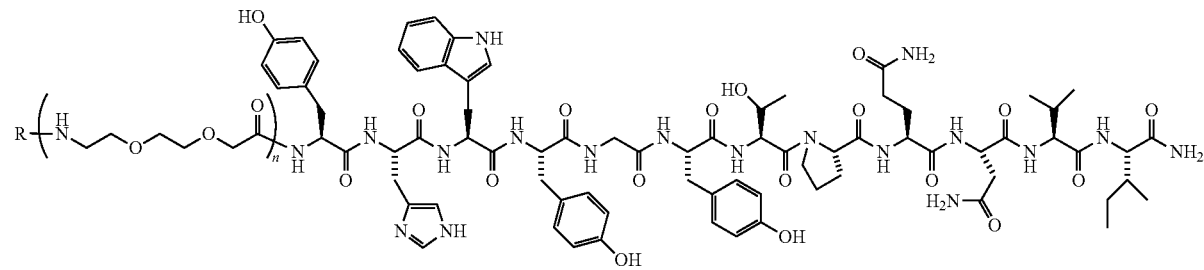

where R is a reporter moiety, such as a NIRF reporter moiety or fluorochrome (e.g., Cy5, Cy5.5, or ZW800-1) and n is an integer from 1 to 3. By way of example the probe can have the following formula:

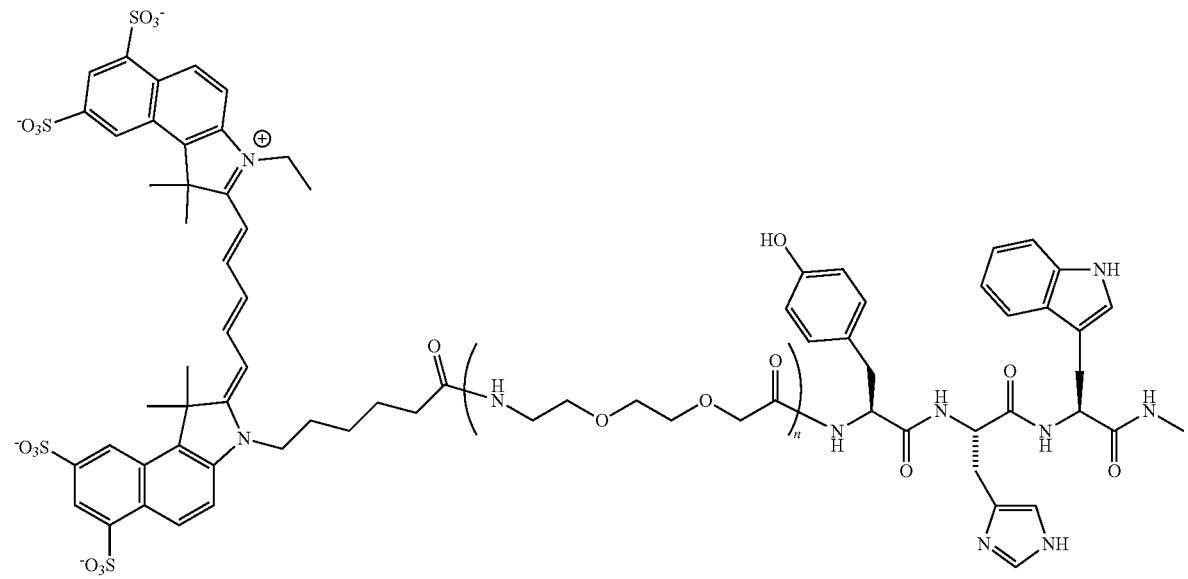

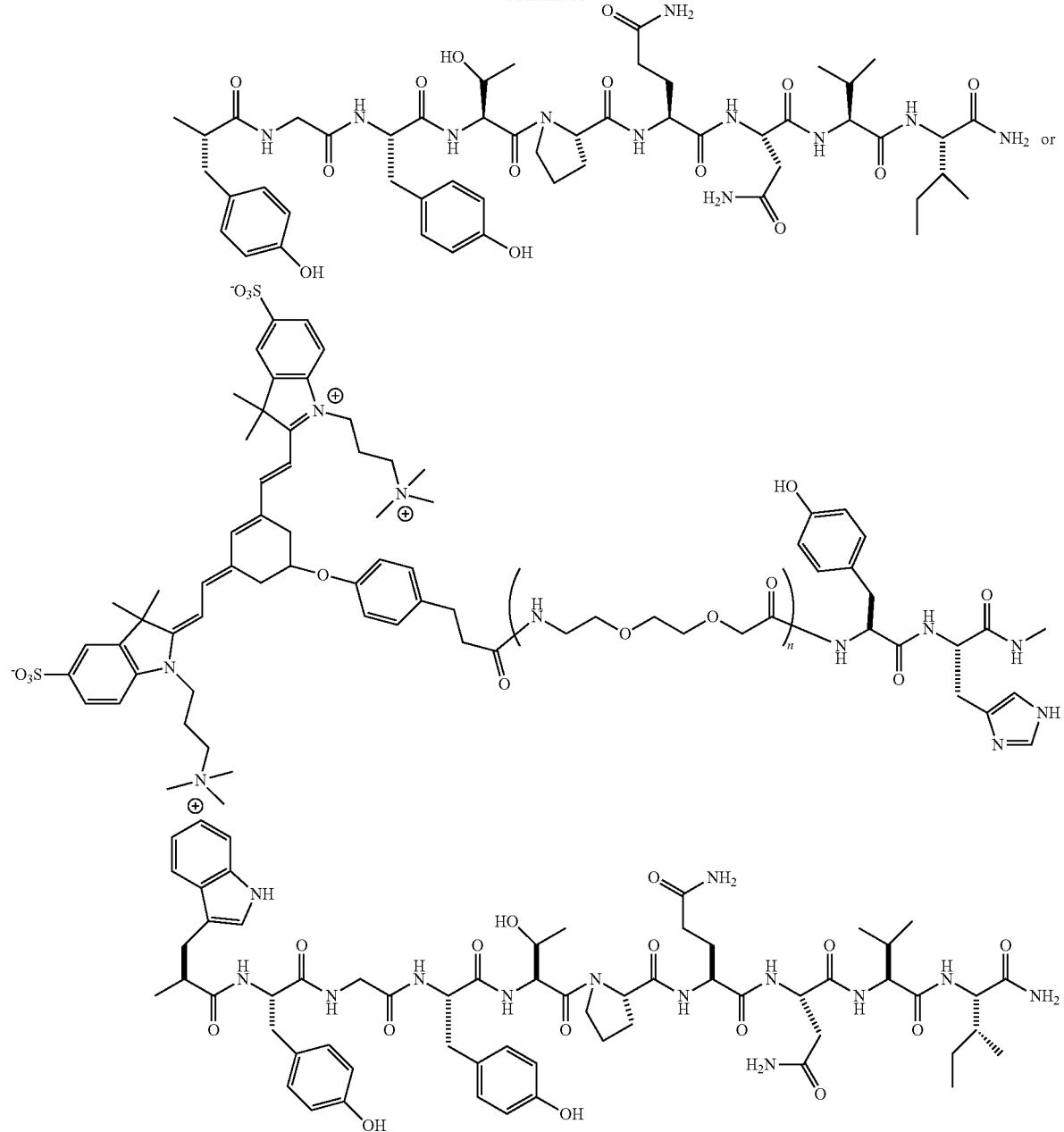
where n is an integer from 1 to 3 (e.g., 1).
In other embodiments, the probe can include the following formula:
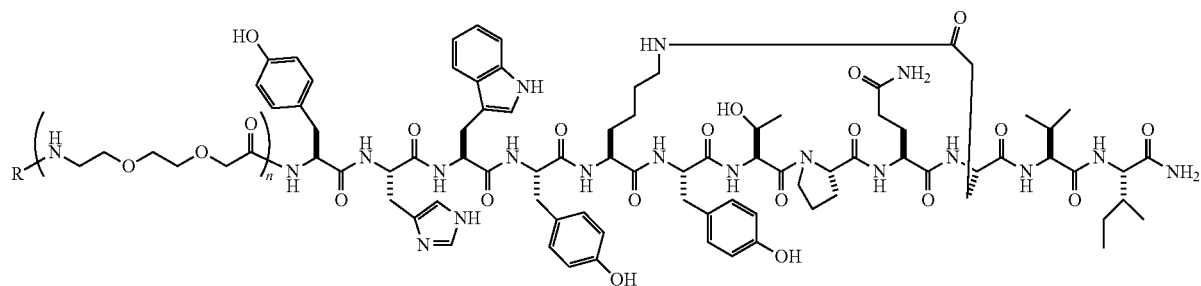

where R is a reporter moiety, such as a NIRF reporter moiety or a fluorochrome (e.g., Cy5, Cy5.5, or ZW800-1) and n is an integer from 1 to 3. By way of example the probe can have the following formula:

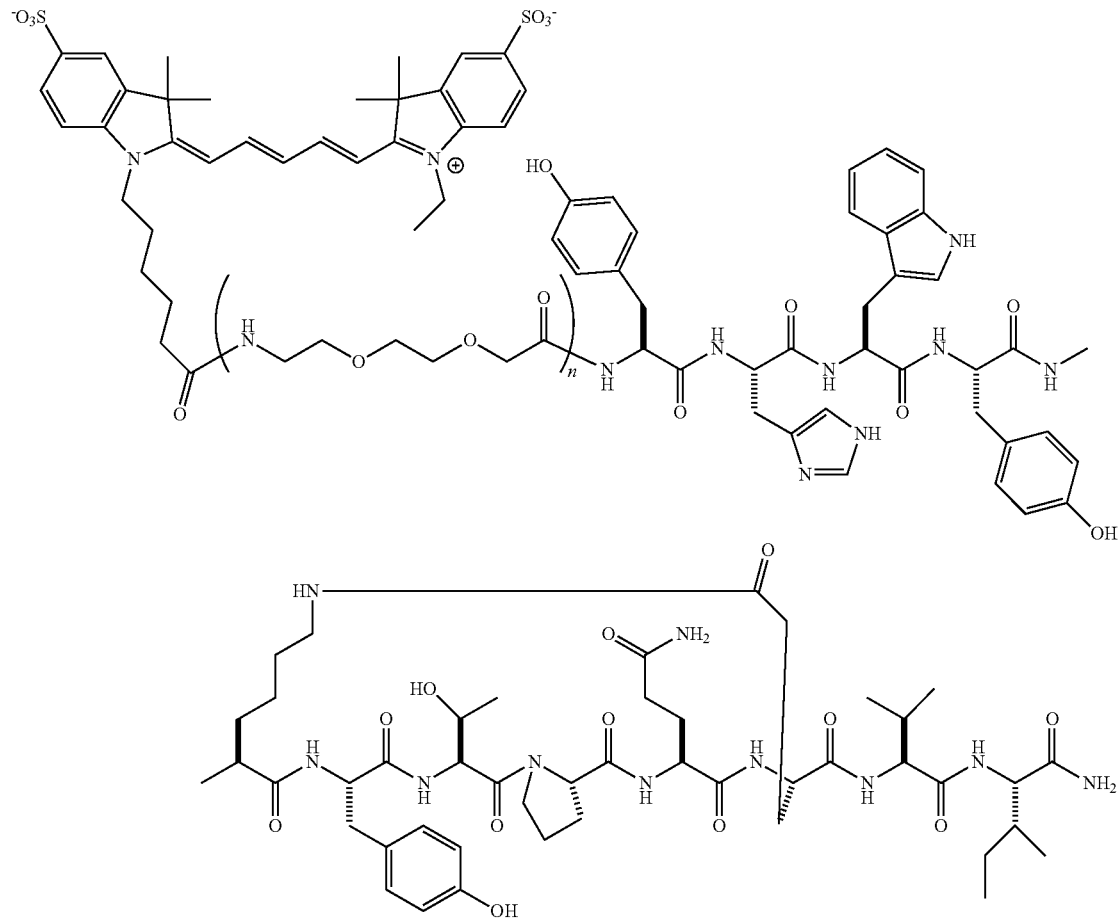

where n is an integer from 1 to 3 (e.g., 1).

BRIEF DESCRIPTION OF THE DRAWINGS

FIGS. 3(A-B) illustrate images showing Gli36Δ5 (A) and U87-MG (B) cells incubated with 1 μmol/L compounds for the indicated times. Uptake of the compounds was assessed using epifluorescence microscopy. Images were taken at ×40 magnification. Scale bar, 50 μm.

FIG. 4 illustrates graphs showing the specificity of the targeting assessed using a scrambled peptide (6) via competition against unlabeled parent peptide compound (5). Subjects bearing orthotopic brain tumors derived from Gli36Δ5 cells over expressing EGFR were treated with (1 nmol/g mice) of compound 6 (n=3) or compound 2 (n=5). Ex vivo analysis of brain tissues showed that compound 2 targets the tumor significantly (***, P>0.0001) more efficiently than the scrambled peptide 6. Representative images of the brain tumors are shown above the corresponding bars (left graph). When subjects bearing orthotopic brain tumors derived from Gli36Δ5 cells over expressing EGFR were cotreated with compound 2 and a 10-fold excess of nonlabeled parent compound 5, the signal over the tumor region was significantly reduced. This suggests that the fluorescence labeling of tumor is specific to the peptide sequence of 2.

FIG. 5 illustrates images showing the colocalization of EGFR-targeted probe with cells expressing high levels of EGFR. Scale bar, 20 mm.

FIGS. 6(A-B) illustrate western blots showing (A) showing the relative levels of wild-type EGFR expressed in Gli36Δ5 and U87-MG glioblastoma cell lysates using an antibody specific to wild-type EGFR (DAKO, cat #M7289); and (B) comparing the mutant EGFRvIII content in Gli36Δ5 and U87-MG tumor cells lines using an EGFRvIII-specific antibody (Bioss Inc., cat #bs-2558R). β-Actin was used a loading control. Densitometry analysis of Western blotting by ImageJ comparing the levels of EGFRvIII in Gli36Δ5 and U87-MG cells show similar content of 1,800 and 2,400 arbitrary units, respectively.

FIGS. 8(A-C) illustrate graphs showing the detected level of the fluorescent agent in (ppmol) administered to live animals (A) or ex vivo brains (B and C) with brain tumors, Gli36Δ5 and U87, using FMT imaging and Maestro imaging (C).

DETAILED DESCRIPTION

Figure 1:
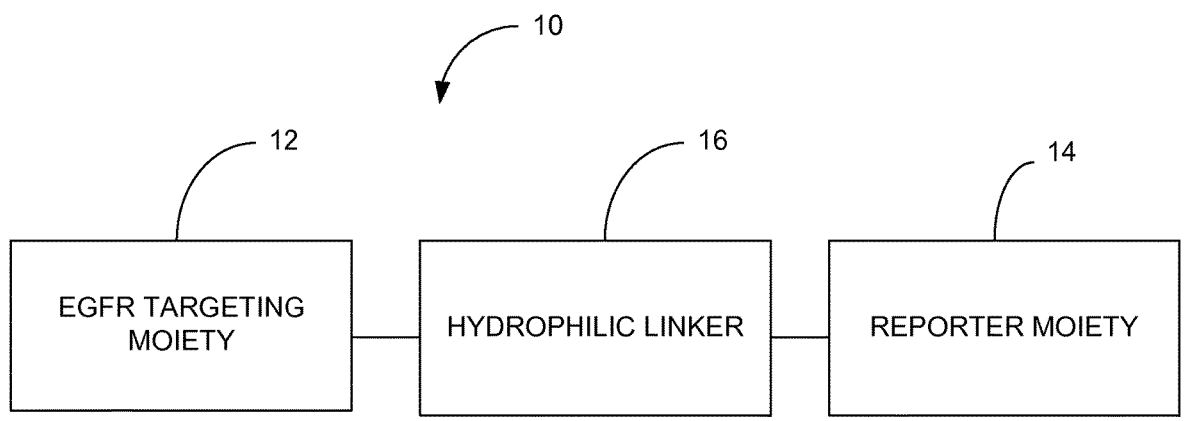
FIG. 1 is a schematic illustration of an imaging probe in accordance with an embodiment of the application.

All scientific and technical terms used in this application have meanings commonly used in the art unless otherwise specified. The definitions provided herein are to facilitate understanding of certain terms used frequently herein and are not meant to limit the scope of the application.

The articles "a" and "an" are used herein to refer to one or to more than one (i.e., to at least one) of the grammatical object of the article. By way of example, "an element" means one element or more than one element.

In the context of the application, the term "sample" can refer to a specimen or culture obtained from any source, as well as clinical, research, biological and environmental samples. Biological samples may be obtained from animals (including humans) and encompass cells, fluids, solids, tissues, and organs, and whole organisms.

As used herein, the term "subject" can refer to any animal including, but not limited to, humans and non-human animals (e.g., rodents, arthropods, insects, fish (e.g., zebrafish)), non-human primates, ovines, bovines, ruminants, lagomorphs, porcines, caprines, equines, or canines felines, ayes, etc.).

As used herein, the terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

As used herein, the terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, meningoma, medulloblastoma, schwannoma and epidymoma.

As used herein, the terms "polypeptide" or "peptide" are used interchangeably and can refer to an oligopeptide, peptide, polypeptide, or protein sequence, or to a fragment, portion, or subunit of any of these, and to naturally occurring or synthetic molecules. The term "polypeptide" can also include amino acids joined to each other by peptide bonds or modified peptide bonds, i.e., peptide isosteres, and may contain any type of modified amino acids. The term can also include peptides and polypeptide fragments, motifs and the like, glycosylated polypeptides, and all "mimetic" and "peptidomimetic" polypeptide forms.

As used herein, the terms "probe" or "imaging probe" can refer to a biological moiety that may be used to detect, image, and/or monitor the presence and/or progression of a cell cycle, cell function/physiology, condition, pathological disorder and/or disease.

As used herein, the term "diagnostically effective amount" can refer to an amount of an imaging composition that is sufficient to enable imaging of at least one cell, tissue, or organism using an imaging modality.

As used herein, the term "targeting moiety" can refer to a molecule or molecules that are able to bind to and complex with a biomarker. The term can also refer to a functional group that serves to target or direct an imaging probe to a particular location, cell type, diseased tissue, or association. In general, a "targeting moiety" can be directed against a biomarker.

As used herein, the term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. In exemplary embodiments, antibodies used with the methods and compositions described herein are derivatives of the IgG class.

As used herein, the term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

As used herein, the term "diabodies" refers to dimeric scFvs. The components of diabodies typically have shorter peptide linkers than most scFvs and they show a preference for associating as dimers.

As used herein, the term "epitope" refers to a physical structure on a molecule that interacts with a selective component. In exemplary embodiments, epitope refers to a desired region on a target molecule that specifically interacts with a selectivity component.

As used herein, the term "Fab" refers to an antibody fragment that is essentially equivalent to that obtained by digestion of immunoglobulin (typically IgG) with the enzyme papain. The heavy chain segment of the Fab fragment is the Fd piece. Such fragments may be enzymatically or chemically produced by fragmentation of an intact antibody, recombinantly produced from a gene encoding the partial antibody sequence, or it may be wholly or partially synthetically produced.

As used herein, the term "Fab'" refers to an antibody fragment that is essentially equivalent to that obtained by reduction of the disulfide bridge or bridges joining the two heavy chain pieces in the F(ab')$_2$ fragment. Such fragments may be enzymatically or chemically produced by fragmentation of an intact antibody, recombinantly produced from a gene encoding the partial antibody sequence, or it may be wholly or partially synthetically produced.

As used herein, the term "F(ab')$_2$" refers to an antibody fragment that is essentially equivalent to a fragment obtained by digestion of an immunoglobulin (typically IgG) with the enzyme pepsin at pH 4.0-4.5. Such fragments may be enzymatically or chemically produced by fragmentation of an intact antibody, recombinantly produced from a gene encoding the partial antibody sequence, or it may be wholly or partially synthetically produced.

As used herein, the term "Fv" refers to an antibody fragment that consists of one $V_H$ and one $V_L$ domain held together by noncovalent interactions. The term "dsFv" is used herein to refer to an Fv with an engineered intermolecular disulfide bond to stabilize the $V_H$-$V_L$ pair.

As used herein, the terms "single-chain Fvs" and "scFvs" refers to recombinant antibody fragments consisting of only the variable light chain ($V_L$) and variable heavy chain ($V_H$) covalently connected to one another by a polypeptide linker. Either $V_L$ or $V_H$ may be the NH$_2$-terminal domain. The polypeptide linker may be of variable length and composition so long as the two variable domains are bridged without serious steric interference. In exemplary embodiments, the linkers are comprised primarily of stretches of glycine and serine residues with some glutamic acid or lysine residues interspersed for solubility.

This application generally relates to compositions and methods for imaging cells, and more particularly to imaging probes for detection or imaging ex vivo or in vivo epidermal growth factor (EGFR) expressing cells. EGFR plays important roles in cell growth, differentiation, and migration. Its positive signaling was found to cause increased proliferation, decreased apoptosis, and enhanced tumor cell motility and angiogenesis. EGFR expression is frequently found in wide spectrum of human tumors of epithelial origin, including non-small cell lung cancer (NSCLC), breast, head and neck (SCCHN), gastric, colorectal, esophageal, prostate, bladder, renal, pancreatic, ovarian, and brain cancers. EGFR can thus be used as a tumor or cancer specific target for receptor-mediated delivery systems of therapeutic agents and imaging probes.

FIG. 1 is a schematic illustration of an imaging probe 10 that can target EGFR expressing cells, such as EGFR expressing cancer cells (e.g., glioblastomas) in accordance with an embodiment described herein. The imaging probe can include an EGFR targeting moiety 12, a reporter moiety 14, and a hydrophilic linker 16 that links or couples the EGFR targeting moiety 12 to the reporter moiety 14.

In some embodiments, the EGFR targeting moiety can be hydrophobic and include a peptide that selectively or specifically binds to EGFR. The peptide can be identified using phage display technology. Phage display technology provides a means for expressing a diverse population of random or selectively randomized peptides. Various methods of phage display and methods for producing diverse populations of peptides are well known in the art. For example, methods for preparing diverse populations of binding domains on the surface of a phage have been described in U.S. Pat. No. 5,223,409. In particular, phage vectors useful for producing a phage display library as well as methods for selecting potential binding domains and producing randomly or selectively mutated binding domains are also provided in U.S. Pat. No. 5,223,409. Similarly, methods of producing phage peptide display libraries, including vectors and methods of diversifying the population of peptides that are expressed, are also described in Smith et al., 1993, Meth. Enzymol., 217:228-257, Scott et al., Science, 249:386-390, and two PCT publications WO 91/07141 and WO 91/07149. Phage display technology can be particularly powerful when used, for example, with a codon based mutagenesis method, which can be used to produce random peptides or randomly or desirably biased peptides (see, e.g., U.S. Pat. No. 5,264, 563). These or other well-known methods can be used to produce a phage display library, which can be subjected to the in vivo phage display method in order to identify a peptide that homes to one or a few selected tissues.

In vitro screening of phage libraries has previously been used to identify peptides that bind to antibodies or cell surface receptors (see, e.g., Smith, et al., 1993, Meth. Enzymol., 217:228-257). For example, in vitro screening of phage peptide display libraries has been used to identify novel peptides that specifically bind to integrin adhesion receptors (see, e.g., Koivunen et al., 1994, J. Cell Biol. 124:373-380), and to the human urokinase receptor (Goodson, et al., 1994, Proc. Natl. Acad. Sci., USA 91:7129-7133).

In certain embodiments, the EGFR targeting moiety can include an EGF peptide ligand that selectively or specifically binds to EGFR expressed by cancer cells. In one example, the EGF peptide ligand can have an amino acid sequence of YHWYGYTPQNVI (SEQ ID NO: 1) (referred to herein as GE 11). GE 11 is a peptide discovered through phage display screening against EGFR.

In other embodiments, the EGFR targeting moiety can be a cyclic analogue of an EGF peptide ligand (e.g., GE 11) that includes a stabilized conformational turn in the peptide. In one example, the cyclic analogue can have an amino acid sequence of YHWY-cyclo[KYTPQE]VI (SEQ ID NO: 2).

The EGFR targeting moiety can include any other molecule, or complex of molecules, which is/are capable of interacting and/or binding with EGFR of the cell. An example of another EGFR targeting moiety is an antibody that selectively or specifically binds to EGFR. The antibody can be a monoclonal antibody, a polyclonal antibody, or a humanized antibody including without limitation: Fv fragments, single chain Fv (scFv) fragments, Fab' fragments, F(ab')2 fragments, single domain antibodies, camelized antibodies and antibody fragments, humanized antibodies and antibody fragments, and multivalent versions of the foregoing; multivalent targeting moieties including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule.

Preparation of antibodies may be accomplished by any number of well-known methods for generating monoclonal antibodies. These methods typically include the step of immunization of animals, typically mice, with a desired immunogen (e.g., a desired target molecule or fragment thereof). Once the mice have been immunized, and preferably boosted one or more times with the desired immunogen(s), monoclonal antibody-producing hybridomas may be prepared and screened according to well known methods. See, for example, Kuby, Janis, Immunology, Third Edition, pp. 131-139, W.H. Freeman & Co. (1997), for a general overview of monoclonal antibody production, that portion of which is incorporated herein by reference.

The reporter moiety linked to the EGFR targeting moiety by the linker region can include any reporter moiety or contrast agent that allows the probe to be detectable upon in vivo, in vitro, or ex vivo administration to a EGFR expressing cell and particularly allows the EGFR expressing cell to be optically imaged in vivo. Examples of such reporter moieties or contrast agents can include isotopic labels, such as a naturally non-abundant heavy isotope or radioactive isotope; optically detectable moieties, such as a chromophore, luminophore, fluorophore, quantum dot or nanoparticle light scattering label; electromagnetic spin label; calorimetric agent; magnetic substance; electron-rich material such as a metal; electrochemiluminescent label; moiety that can be detected based on a nuclear magnetic, paramagnetic, electrical, charge to mass, or thermal characteristic; light scattering or plasmon resonant materials, such as gold or silver particles; or multielement reporter systems, such as affinity tags including but not limited to enzyme and substrate reporter groups, and dinitrophenyl (DNP) reporter group and fluorophore labeled anti-DNP antibody and the like. Fluorophores that can potentially be used include, for example, fluorescent lanthanide complexes, including those of Europium and Terbium, fluorescein, fluorescein isothiocyanate, dichlorotriazinylamine fluorescein, rhodamine, tetramethylrhodamine, umbelliferone, eosin, erythrosin, coumarin, methyl-coumarins, pyrene, Malacite green, Cy3, Cy5, Cy5.5, ZW800-1 (i.e., N-hydroxysuccinimide (NHS) ester), stilbene, Lucifer Yellow, Cascade Blue, Texas Red, alexa dyes, dansyl chloride, phycoerythin, luciferin, green fluorescent protein and its wavelength shifted variants, bodipy, and others known in the art such as those described in Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999), or WO 98/59066.

In a particular embodiment, the reporter moiety can include a near infrared fluorescence (NIRF) imaging moiety or fluorochrome, such as Cy3, Cy5, Cy5.5, or ZW800-1, that can be linked to the EGFR targeting moiety with the hydrophilic linker.

The hydrophilic linker that links or couples the EGFR targeting moiety to the reporter moiety can include any linker, chemical, and/or or biological moiety that enhances solubility of the probe in an aqueous media and enhances the binding affinity of the EGFR targeting moiety to EGFR. The linker can be of any suitable length and contain any suitable number of atoms and/or subunits. Advantageously, the linker region is sufficiently long and hydrophilic to offset the hydrophobicity of the EGFR targeting moiety. In one example, the linker can comprise a monomer, dimer, or oligomer PEG linker. The PEG linker can be attached to a hydrophobic EGFR targeting moiety and reporter moiety in various lengths.

In some embodiments, a probe for imaging and/or detecting an EGFR expressing cell can include a near infrared fluorescence (NIRF) or fluorochrome reporter moiety coupled to a EGF peptide ligand (e.g., GE11) by a linker. The NIRF reporter moiety or fluorochrome can be, for example, Cy5, Cy5.5, ZW800-1, and the linker can be a PEG linker, such as an amino-ethoxy-ethoxy-acid linker.

In one example, the probe can include the following formula:

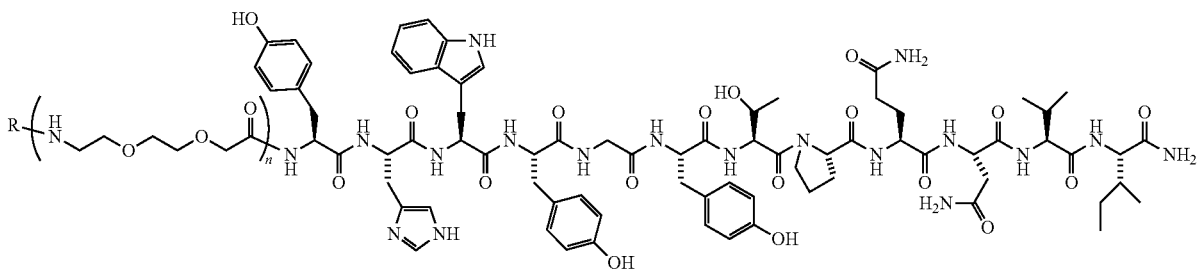

where R is a reporter moiety, such as a NIRF reporter moiety or fluorochrome (e.g., Cy5, Cy5.5, or ZW800-1) and n is an integer from 1 to 3. By way of example the probe can have the following formula:

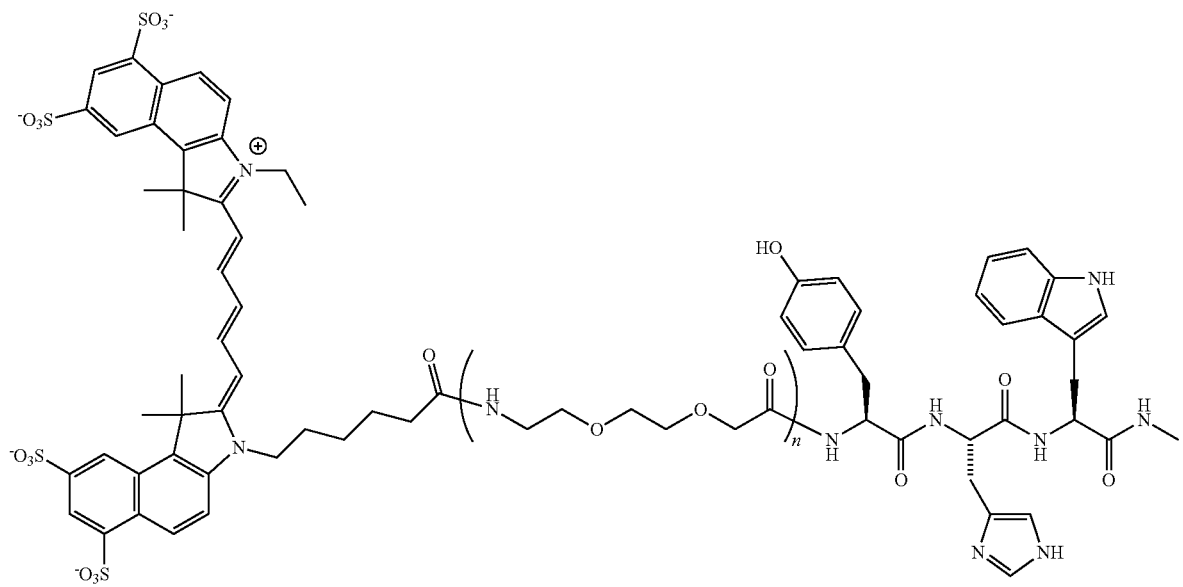
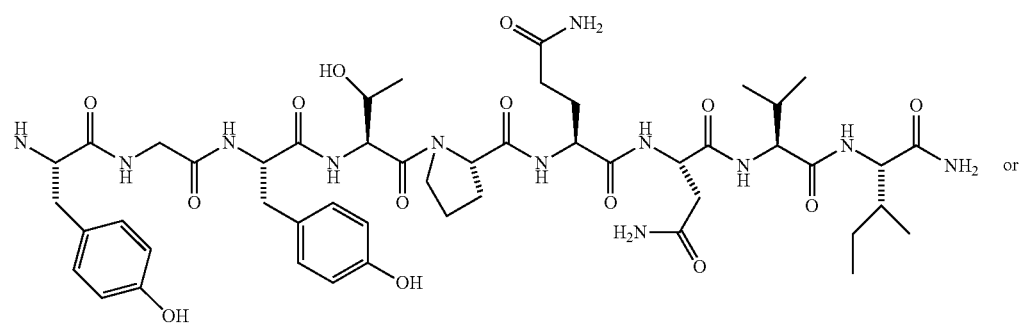
or
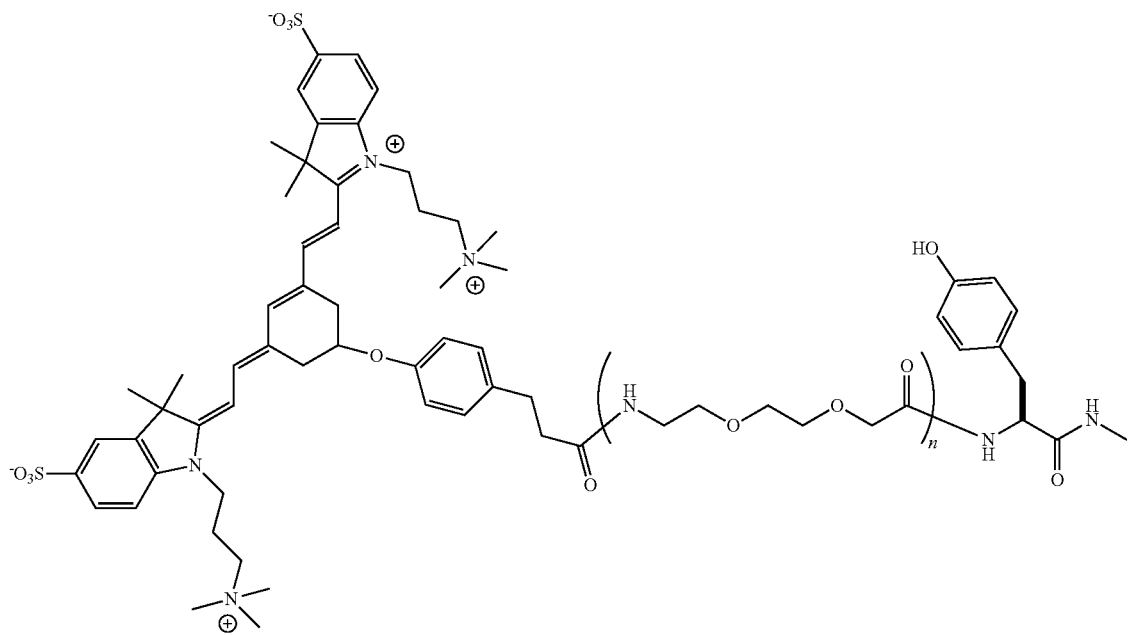

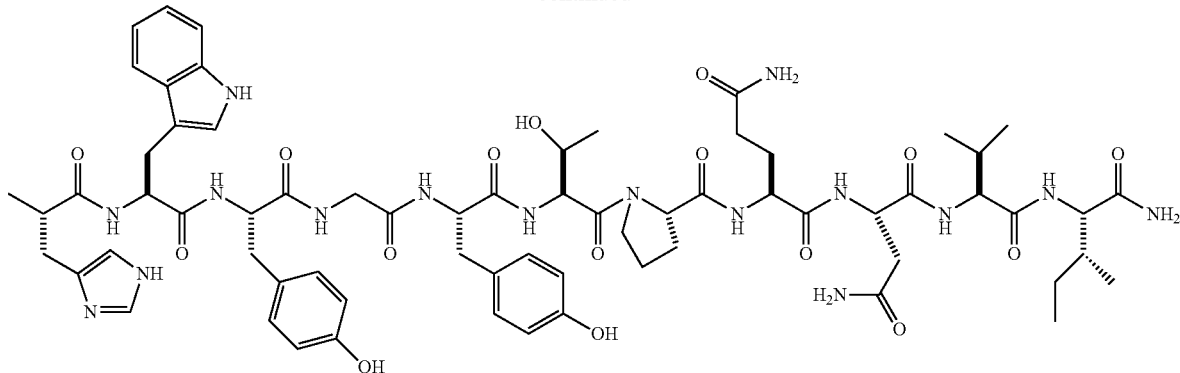

where n is an integer from 1 to 3 (e.g., 1).

In other embodiments, a probe for imaging and/or detecting an EGFR expressing cell can include a near infrared fluorescence (NIRF) or fluorochrome reporter moiety coupled to a cyclic analogue of EGF peptide ligand by a linker. The NIRF reporter moiety or fluorochrome can be, for example, Cy5, Cy5.5, ZW800-1, and the linker can be a PEG linker, such as an amino-ethoxy-ethoxy-acid linker.

In one example, the probe can include the following formula:

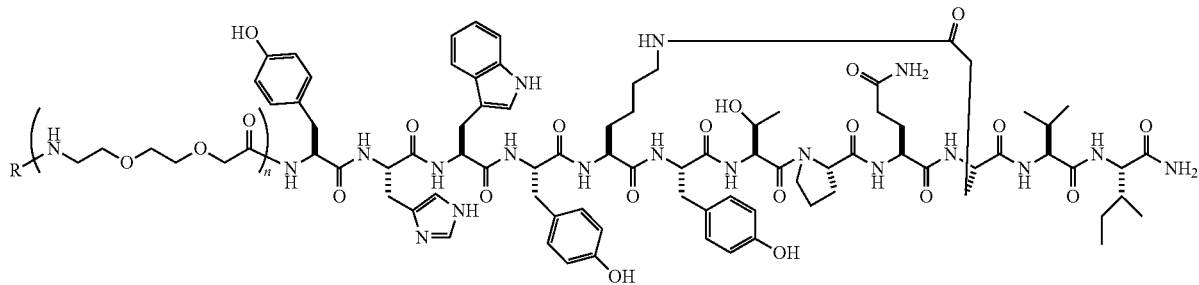

where R is a reporter moiety, such as a NIRF reporter moiety or a fluorochrome (e.g., Cy5, Cy5.5, or ZW800-1) and n is an integer from 1 to 3. By way of example the probe can have the following formula:

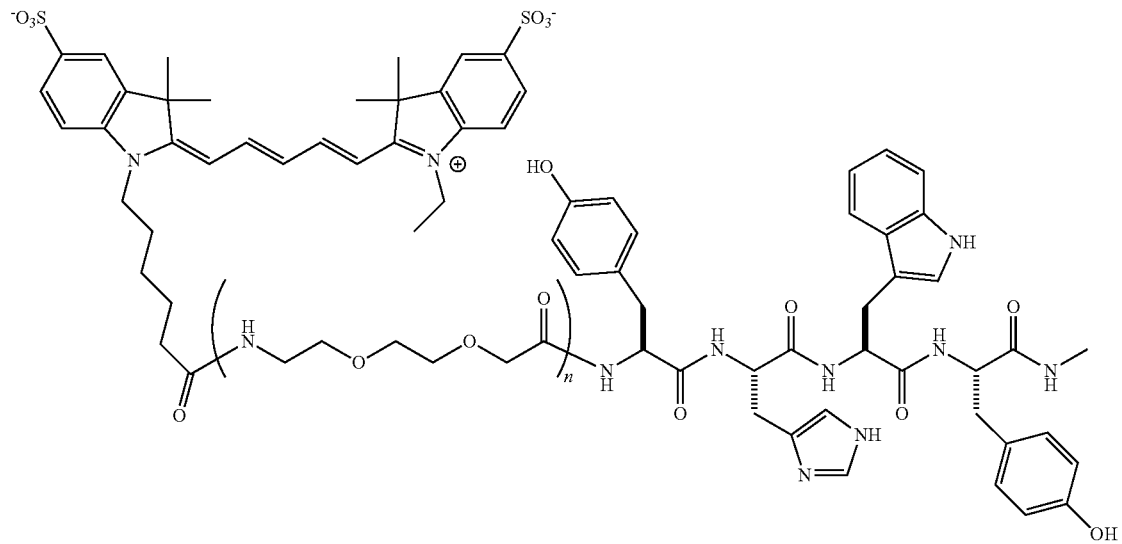

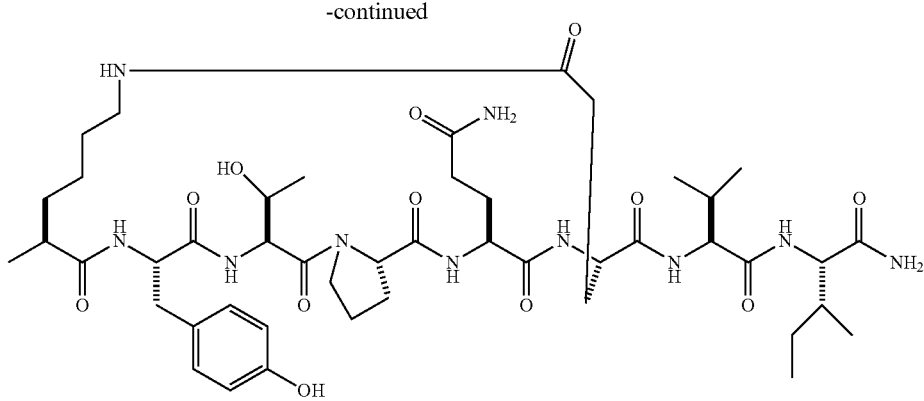

where n is an integer from 1 to 3 (e.g., 1).

In some embodiments, the probe can be used to detect cancer cells expressing EGFR at relatively short time scale and distinguish between cancer cells with high and low expression levels. Depending upon the particular application, the cell may be in vivo or ex vivo. Ex vivo cells can be collected as part of one or more samples using one or a combination of known techniques (e.g., biopsy) and, if needed, further processed (e.g., centrifuged) prior to culture, analysis, etc. The probe can be applied (e.g., topically) to the collected cells and used, for example, in immunohistochemistry assays to determine whether the collected cells express EGFR.

To detect an EGFR expressing cell in vivo, a diagnostically effective amount of the probe can be administered to a subject. Methods of introduction include, but are not limited to, topical, local, intradermal, intramuscular, intraperitoneal, intravenous, subcutaneous, intranasal, rectal, vaginal, and oral routes. The probe may be administered by any convenient route, such as by infusion or bolus injection or by absorption through epithelial or mucocutaneous linings (e.g., oral mucosa, vaginal, rectal and intestinal mucosa, etc.), and may be administered together with other biologically active agents. The probe may be introduced into the central nervous system by any suitable route, including intraventricular injection, intrathecal injection, or intraventricular injection via an intraventricular catheter that is attached to a reservoir.

The probe can be delivered systematically (e.g., intravenously), regionally, or locally (e.g., intra- or peri-tumoral injection) by, for example, intra-arterial, intra-tumoral, intravenous, parenteral, intra-pneural cavity, topical, oral or local administration, as well as subcutaneous, intra-zacheral (e.g., by aerosol), or transmucosal (e.g., voccal, bladder, vaginal, uterine, rectal, nasal, mucosal). If delivery of the probe to the brain is desired, probe can be injected into an artery of the carotid system of arteries (e.g., occipital artery, auricular artery, temporal artery, cerebral artery, maxillary artery etc.).

The amount of the probe sufficient to provide the desired result(s) will depend on a variety of factors, such as the amount required to avoid undesirable physiological results. The precise dose to be employed can also depend on the route of administration, and should be decided according to the judgment of a medical practitioner and each subject's circumstances. In addition, known in vitro and in vivo assays may optionally be employed to help identify optimal dosage ranges. Effective doses may be extrapolated from dose-response curves derived from in vitro or in vivo test systems.

The probe can be administered in a variety of unit dosage forms, depending upon the particular cell or tissue being imaged, the general medical condition of each subject, the method of administration, and the like. Details on dosages are well described in the scientific literature. The exact amount and concentration of the imaging composition, or the "effective dose", can be routinely determined (e.g., by a medical practitioner). The "dosing regimen" will depend upon a variety of factors, such as whether the cell or tissue to be imaged is disseminated or local, the general state of the subject's health, the subject's age, and the like. Using guidelines describing alternative dosing regimens, e.g., from the use of other imaging agents and compositions, the skilled artisan can readily determine by routine trials the optimal effective concentrations of the imaging composition.

In another example, the probe can be used as part of an intra-operative molecular imaging (IOI) procedure, such as disclosed in U.S. patent application Ser. No. 11/811,818 to Basilion, to detect abnormal EGFR expressing cells and/or diseased tissue. To identify and facilitate removal of abnormal EGFR expressing cells, for example, microscopic MI techniques can be combined with topically applied probes described herein. Thus, the probe can be delivered via topical application, as opposed to intravenous injection, which facilitates localized diffusion of the imaging probes. In one example, the imaging probe can be combined with IOI to identify malignant cells that have infiltrated and/or are beginning to infiltrate at a tumor brain margin. The method can be performed in real-time during brain or other surgery. The method can include topical application of an imaging probe. An imaging modality can then be used to detect and subsequently gather image data. The resultant image data may be used to determine, at least in part, a radiological treatment. Alternatively, this image data may be used to control, at least in part, an automated surgical device (e.g., laser, scalpel, and micromachine) or to aid in manual guidance of surgery. Further, the image data may be used to plan and/or control the delivery of a therapeutic agent (e.g., by a micro-electronic machine or micro-machine).

In another aspect, the present application provides a method for treating a disease in a subject. One step of the method can include contacting the EGFR expressing cell with a diagnostically effective amount of the imaging probe. Upon contacting the imaging probe with the cell, one or more imaging modalities can be used to detect the reporter moiety to produce a molecular signature of the cell or differentiate the cell. Based on the molecular signature of the cell, the subject can then be appropriately treated for the particular disease by, for example, administering an effective amount of a therapeutic composition. An "effective amount" can refer to that amount of a therapeutic agent that results in amelioration of symptoms or a prolongation of survival in the subject and relieves, to some extent, one or more symptoms of the disease or returns to normal (either partially or completely) one or more physiological or biochemical parameters associated with or causative of the disease. Therapeutic agents can include any agent (e.g., molecule, drug, pharmaceutical composition, etc.) capable of preventing, inhibiting, or arresting the symptoms and/or progression of a disease.

In one example of the application, a molecular signal of a cell can indicate that a subject has a particular cancer. Because the type, severity, and stage of the cancer can be determined based on the molecular signature of the cell, the subject can then be administered an effective amount of a chemotherapy agent to treat the cancer. Chemotherapy agents are well known in the art and can include, for example, alkylating agents (e.g., cyclophosphamide, ifosfamide), antibiotics that affect nucleic acids (e.g., doxorubicin, bleomycin), platinum compounds (e.g., cisplatin), mitotic inhibitors (e.g., vincristine), antimetabolites (e.g., 5-fluorouracil), camptothecin derivatives (e.g., topotecan), biological response modifiers (e.g., interferon), and hormone therapies (e.g., tamoxifen).

Alternatively, the imaging probe can be used in a method to identify cells that are treatable by a particular therapeutic agent or therapeutic intervention. Additionally, the imaging probe can be used to the progress of therapy by monitoring a decreasing signal over time.

The following examples are for the purpose of illustration only and are not intended to limit the scope of the claims, which are appended hereto.

Example 1

In this Example, we synthesized different versions of an imaging agent by varying the length of polyethylene glycol (PEG) linker between a 12-residue linear peptide sequence, GE11 (YHWYGYTPQNVI) (SEQ ID NO: 1) and a fluorochrome, Cy5.5. These imaging compounds were then tested in tissue culture cells lines expressing different levels of the EGFR and in orthotopic brain tumors generated from the cell lines. It was determined that the length of the linker critically affected the efficacy of the agent both in tissue culture and in the in vivo setting. Furthermore, these agents were capable of discriminating tumors expressing different levels of EGFR in orthotopic GBM models.

Materials and Methods
Probe Synthesis and Analysis

The peptides were synthesized manually using protocols previously described. Peptide was labeled in solution with monoreactive Cy5.5 NHS ester (CyDye, GE Healthcare). Crude fluorophore-labeled peptides were purified by reversed phase high-performance liquid chromatography (RP-HPLC). The isolated peak was lyophilized and characterized matrix-assisted laser desorption/ionization (MALDI) mass spectrometry was done under positive mode. Compounds are characterized by RPHPLC under 2 different conditions and by thin layer chromatography with 3 different solvent conditions. Concentration of stock Cy5.5-labeled peptide solutions in dimethyl sulfoxide (DMSO) was determined by UV-Vis spectrometry [Cy5.5 molar extinction coefficient is 250,000 $(mol/L)^{-1} cm^{-1}$ at 675 nm].

Cell Culture

Human glioblastoma astrocytoma, an epithelial-like cell line U87-MG, and human glioblastoma cell line stably over expressing the EGFRvIII-mutant form of the egfr gene, Gli36Δ5, were used in these studies. U87-MG and A431 cells were recently obtained from American Type Culture Collection. Gli36Δ5 cells were obtained from E. A. Chiocca and were authenticated by Research Animal Diagnostic Laboratory at the University of Missouri (Columbia, Mo.) for interspecies and mycoplasma contamination by PCR analysis. Cell lines were maintained in RPMI or Dulbecco's Modified Eagle's Medium (DMEM; Gibco), respectively, and supplemented with 10% FBS and 1% penicillin-streptomycin. The cells were incubated at 37° C. in a humidified 5% $CO_2$ atmosphere. For Gli36Δ5 cells, puromycin was also included to maintain the expression of the EGFRvIII plasmid.

Saturation Binding Assays

To determine binding affinities of the Cy5.5-labeled peptides 1 to 4 to EGFR, a saturation binding assay protocol using labeled fluorescence ligand against cell surface receptors was adapted as previously reported. Briefly, Gli36Δ5 cells were plated 20,000 cells per well were plated on black Costar 96-well plates (cat. no. 3603). Probes were diluted to range of concentration (0-25 mmol/L) in growing media with 0.3% bovine serum albumin (BSA) and added into wells and incubated at 37° C. for 90 minutes at 5% $CO_2$. Cells were then washed with PBS twice and dried. DMSO was added before reading fluorescence (excitation 670 nm, emission 700 nm) with a Tecan Infinite M200 plate reader. Saturation binding assay data were in quadruplicates and analyzed using one site binding classical equation for non-linear regression analysis with the GraphPad Prism version 4.0.

Receptor Uptake Immunofluorescence

Gli36Δ5 or U87-MG cell lines plated in 96-well culture plates (20,000 cells per well; 3 wells per condition) were incubated over indicated time periods with 1 mmol/L of Cy5.5-labeled EGF peptides 2, 3, and 4 at 37° C. and 5% $CO_2$. Cells were briefly rinsed with HEPES buffer and imaged with a Tecan Infinite M200 fluorescence plate reader (excitation 670 nm, emission 700 nm).

Immunocytochemistry of Cells Grown on Coverslips

Gli36Δ5 or U87-MG cancer cell lines were plated on coverslips and incubated overnight to promote adherence. The cells were then fixed with 4% paraformaldehyde, rinsed with PBS, and blocked with 1% host serum for 30 minutes at room temperature. Coverslips were incubated with primary antibody at room temperature for 2 hours. Antibodies used were mouse anti-human wild-type EGFR (1:100 dilution; clone DAK-H1-WT, Dako cat. no. M7289). The coverslips were then rinsed with PBS and counterstained with 40,6-diamidino-2-phenylindole (DAPI) for 10 minutes at room temperature to visualize the nuclei. After a final rinse with PBS, the coverslips were mounted using Fluor-Mount aqueous media, sealed with nail polish, and observed using epifluorescence microscopy.

Orthotopic Brain Tumor Model

NIH athymic nude female mice (5-8 weeks and 20-25 g upon arrival, NCI-NIH) were maintained at the Animal Resource Center at Case Western Reserve University (Cleveland, Ohio) according to institutional policies. Cell for brain implantation were harvested with 1 mL 0.05% trypsin-EDTA (Gibco) and briefly washed with PBS. Trypsin was inactivated by the addition of serum-containing media. The resulting cell suspension was centrifuged at 1,000 μg for 3 minutes. The cell suspension was centrifuged and the supernatant was removed after 2 washes in PBS. Finally, the cells were resuspended in 2 mL PBS for brain implants per animal (250,000 cells per animal for brain implants). Immediately following the cell harvesting procedure, animals were inoculated. For brain tumor implantation, mice were anesthetized by intraperitoneal (i.p.) injection of 50 mg/kg ketamine/xylazine and fitted into a stereotaxic rodent frame (David Kopf Instruments). A small incision was made just lateral to midline to expose bregma suture. A small (1.0 mm) burr hole was drilled at anterior (AP)=+1, lateral (ML)=−2.5 from the bregma. Glioblastoma cells were slowly deposited at a rate of 1 μL/min in the right striatum at a depth of 3 mm from dura with a 10-μL syringe (23-G needle). The needle was slowly withdrawn and the incision was closed with 2 to 3 sutures. Brain tumors grew for 10 to 12 days as per IACUC protocols at which point in vivo imaging studies were conducted. As control for the effects of surgical intervention, animals were also subjected to the implantation procedure but Optical Imaging of Tumors with EGFR Overexpression received 2 μL PBS (sham animals). Animals were fed exclusively on a special rodent diet (Harlan Laboratories, Inc.; Tekland 2018S) to reduce autofluorescence.

In Vivo and Ex Vivo Fluorescence Imaging

Mice bearing brain tumors derived from Gli36Δ5 or U87-MG cells were administered with compounds at 1 nmol/g via tail vein injection. In vivo competition assays were done with mixture of compound 2 and 10-fold concentration of nonlabeled probe 5. Before injection, mice were anesthetized with isoflurane and subjected to tomographic and spectral fluorescence imaging. One hour after injection, animals were re-imaged. Brains were then extracted and imaged. The excised brains were embedded in Tissue-Tek optimum cutting temperature for cryosections for immunohistochemistry (IHC). Fluorescence-mediated molecular tomography (FMT) images were obtained using FMT2500 (Perkin-Elmer), and 3-dimensional reconstructions of fluorescent signals were acquired using the accompanying software TrueQuant. Quantitative fluorescent signals for Cy5.5 of compound 2 were calibrated as per manufacturer's instructions using the 680-channel. Region of interest (ROI) assigned on the basis of the precise placement of cells during implantation at 3 to 4 mm into the brain. ROI was corroborated with fluorescent signals from ex vivo imaging. Fluorescent multispectral images were obtained using the Maestro In-Vivo Imaging System (CRi, Inc.). The yellow filter set appropriate for Cy5.5 was used for emission and excitation light. The tunable filter was automatically stepped in 10-nm increments whereas the camera captured images at a constant exposure of 200 ms. Fluorescence images were acquired before treatment, immediately after and 1.5 hours after treatment. To compare signal intensities, ROIs were selected over the tumor or nontumor areas, and the change in fluorescence signal over baseline was determined. The spectral fluorescent images consisting of autofluorescence spectra and imaging probe were captured and unmixed on the basis of their spectral patterns. The total signal in the ROI defined in photons measured at the surface of the animal was divided by the area (in pixels). Spectral libraries were generated by assigning spectral peaks to background and fluorescence probe on tissue. The spectral libraries were manually computed using the Maestro software, with each tissue used as its own background control.

IHC of Cryosection of Brain Tissue

Sections (2 mm) of whole mouse brains implanted with Gli36Δ5 cells were fixed with 4% paraformaldehyde, cryosectioned onto microscope slides, rinsed with PBS, and blocked with 1% host serum for 30 minutes at room temperature. Sections were incubated with primary antibody at room temperature for 2 hours. Antibodies used were mouse anti-human wild-type EGFR (1:100 dilution; clone DAK-H1-WT, Dako cat. no. M7289). The coverslips were then rinsed with PBS and counterstained with DAPI for 10 minutes at room temperature to visualize the nuclei. After a final rinse with PBS, the slides were mounted with coverslips using Fluor-Mount aqueous media, sealed with nail polish, and observed using epifluorescence microscopy.

Western Blotting

Cell extracts (50 μg) were fractionated using SDS-PAGE and transferred onto a nitrocellulose membrane. Immunoblotting was done using a 1:500 dilution of an antibody against wild-type EGFR (DAKO, DAK-H1-WT) or a 1:500 dilution of a specific antibody against mutant EGFRvIII (Bioss Inc., cat #bs-2558R). Horseradish peroxidase-conjugated secondary antibodies against mouse IgG (Chemicon) or rabbit IgG (Amersham) were used. Bands were detected using an enhanced chemiluminescence detection system (Pierce).

Statistical Analysis

Analyses of data were achieved with GraphPad Prism version 4.00, GraphPad Software. Binding affinity was determined with nonlinear regression analysis with one site binding hyperbola with an equation: $Y=B_{max} \times X(K_d+X)$, where $B_{max}$ is the maximal binding site and the $K_d$ is the concentration required to reach half-maximal binding. ANOVA analysis at 95% confidence interval (CI) was used to compare treatments (*, P>0.05; , P>0.01; confidence interval, *, P>0.001). To compare live animal FMT, nonparametric one-way ANOVA analyses (Kruskal-Wallis tests) and the median differences were considered significant with P=0.0220.

Results

The goal of these studies was to develop a peptide based NIRF probe that would cross the BBTB and selectively bind to brain tumor cells over expressing EGFR. For these studies, we used a peptide discovered through phage display screening against purified human EGFR. The peptide was modified to include linkers and a NIRF dye. To determine the optimal space between the NIRF dye and the peptide, we designed and synthesized a series of peptides to include increasing numbers of discrete ethylene glycol units to serve as linkers between a Cy5.5 and the N-terminal end of the peptide. Cy5.5 and EGFpep were either directly linked or linked via 1, 2, or 3 units of discrete ethylene glycol (AEEA) moieties (Table 1). To determine which of the compounds optimally interacts with cells expressing EGFR, the apparent binding for each bioconjugate was fluorometrically determined from a saturation binding assay in vitro using a human GBM cell line overexpressing EGFR and Gli36Δ5 (Table 1). Compounds 1, 2, 3, and 4 all bound to the cells with affinities in the micromolar range. Compound 2, which had one linker, had the highest apparent affinity with a $K_d$ at least 2-fold better than compound 1, which had no ethylene linker, 8.9 to 18.5 μmol/L respectively. Compounds 3 and 4 have weaker affinities with $K_d$ of 64.4 and 123.0 μmol/L, respectively.

TABLE 1

The sequences of the peptides studied and the corresponding apparent binding affinities ($K_d$) from saturation binding assays

| Compound | Peptide (EGF$_{pep}$) | $K_d$, μmol/L |
|---|---|---|
| 1 | Cy5.5-YHWYGYTPQNVI-amide | 18.5 ± 3.9 |
| 2 | Cy5.5-(AEEA)$_1$-YHWYGYTPQNVI-amide | 8.9 ± 3.7 |
| 3 | Cy5.5-(AEEA)$_2$-YHWYGYTPQNVI-amide | 64.4 ± 24.6 |
| 4 | Cy5.5-(AEEA)$_3$-YHWYGYTPQNVI-amide | 123.0 ± 174.0 |
| 5 | YHWYGYTPQNVI-amide (GE11-amide) | ND |
| 6 | Cy5.5-(AEEA)$_1$-NYQTPVYGWIYH-amide scrambled | ND |

Abbreviation: ND, not determined

Figure 2:
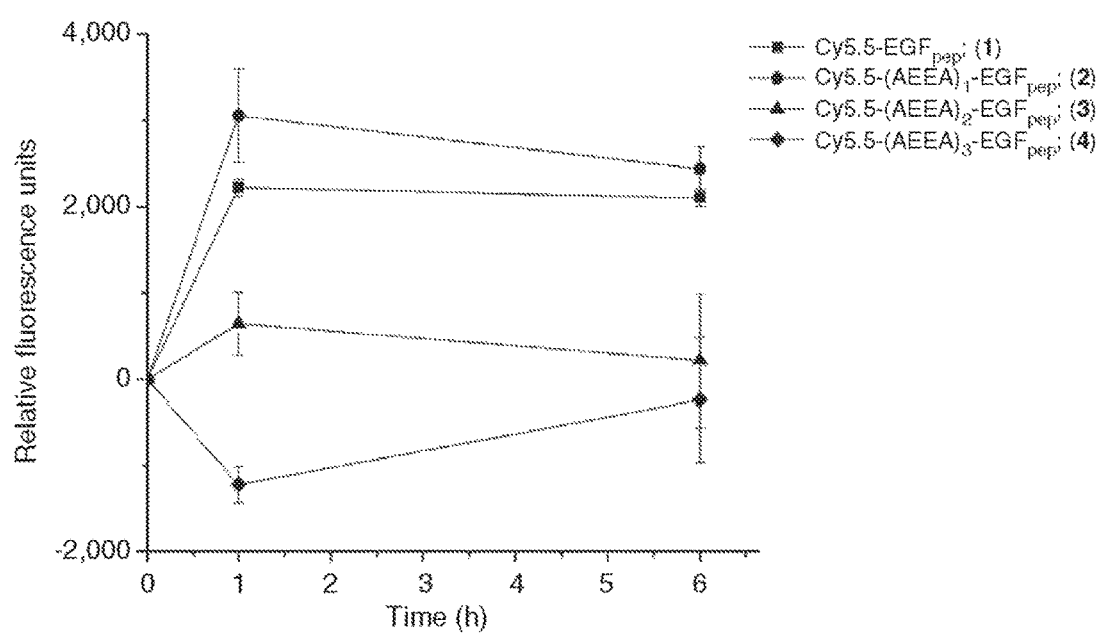
FIG. 2 illustrates a plot showing cell associated fluorescence measured using spectrofluorometry at the indicated times for Gli36Δ5 cells incubated with 1 μmol/L of compounds 1 to 4 [Cy5.5-(AEEA)$_n$-EGF$_{pep}$].

We next used immunofluorescence microscopy to determine the fate of the peptide complexes once they bound to glioblastoma cells expressing EGFR. As predicted from the affinity measurements compound 2, which had the highest affinity, also showed the greatest accumulation of fluorescence after incubation with Gli36Δ5 cells (FIG. 2). Neither compound 1 (no linker) nor either of the molecules with greater linker numbers (compounds 3 and 4) was taken up by the cells to the same extent as compound 2. Interestingly, the peptide with the longest linker and the worst binding affinity, compound 4, was taken up by cells better than compound 3 (FIG. 3A). When tested against U87-MG cells, which express much lower levels of the EGFR, no cellular uptake for any of the compounds was observed (FIG. 3B).

We next tested the ability of these compounds to target EGFR-expressing tumors implanted within the brains of mice. For these studies, mice were orthotopically implanted with Gli36Δ5 cells. Approximately 10 days after implantation, the animals were administered 1 nmol/g via tail vein injection and sacrificed 1 hour later. Brains were harvested and imaged ex vivo for accumulation of the imaging probe. As a control for specificity, we synthesized a Cy5.5-labeled scrambled peptide, compound 6, using the amino acid residues of the parent peptide (compound 5) in random order. Compound 2 targeted the tumor efficiently, accumulating 1.1% of injected dose (FIG. 3A, left graph). In contrast, compound 6 did not target the tumor with delivery of only 0.006% of the injected dose. To further assess specificity, animals that bore Gli36Δ5 brain tumors were administered compound 2 alone or in the presence of a 10-fold excess of unlabeled peptide (compound 5). In animals that received only compound 2, there was significant tumor-associated fluorescence. In contrast, when a 10-fold excess of competitor peptide was coadministered with compound 2, there was approximately a 60% decrease in accumulation of the probe, (FIG. 4A, right graph). Imaging and quantification of identical ROIs taken on the contralateral brain showed little uptake of the probe (data not shown).

To show that the uptake was associated with human EGFR expression on the Gli36Δ5 cells, the resected brains were fixed and subjected to IHC with monoclonal antibodies specific for human EGFR (FIG. 5B). These results have shown that only cells that expressed human EGFR were associated with Cy5.5 fluorescence. Notably, no Cy5.5 signal was associated with surrounding mouse brain.

Figure 7:
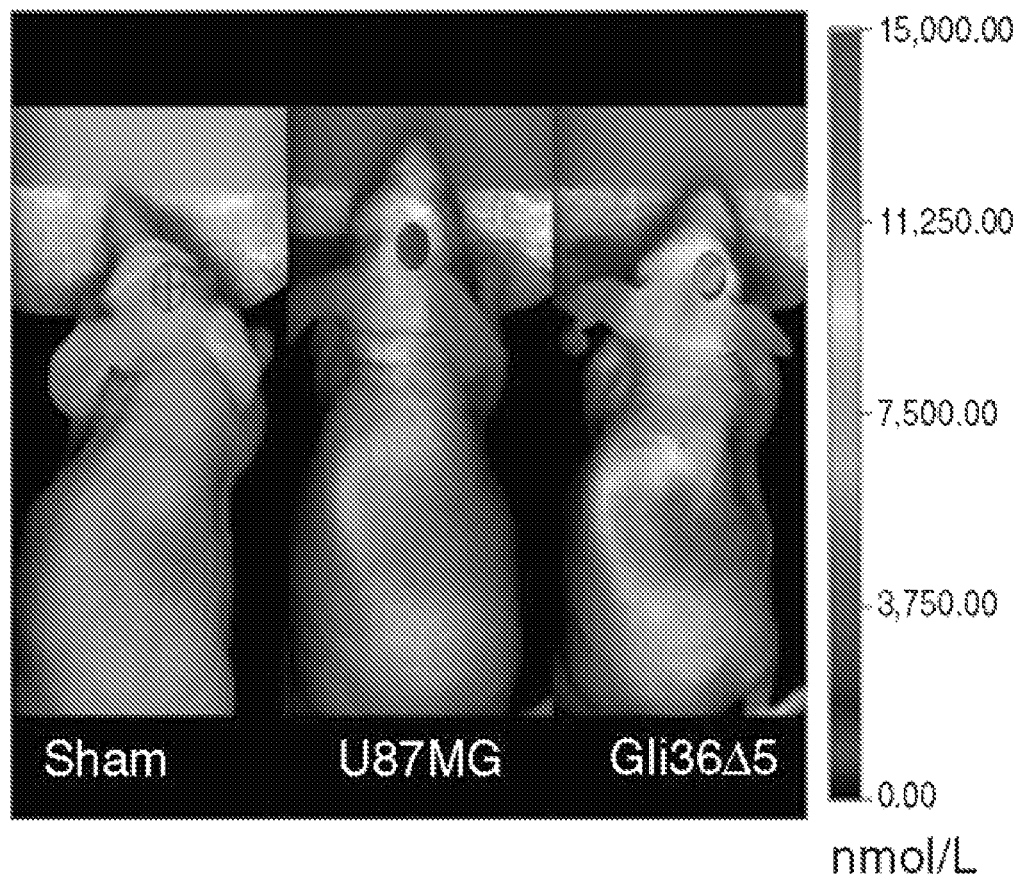
FIG. 7 illustrates an image of FMT3-dimensional reconstruction showing the targeting of compound 2 to brain Gli36Δ5 orthotopic brain tumors. Sham, U87-MG, and Gli36Δ5 shows 272, 1,608, and 9,271 nmol/L amounts of fluorescence in the matching ROIs.

Our final test for compound 2 was to determine whether it would be useful for noninvasive in vivo detection and discrimination of tumors differentially expressing EGFR. For these studies, mice were orthotopically implanted with either Gli36Δ5 cells, which express high EGFR, or U87-MG cells, which express relatively low EGFR levels (FIG. 6A). Following implantation, the tumors were allowed to grow approximately 10 to 12 days and then mice were administered 1 nmol/g of compound 2 via tail vein injection. One hour after injection, the mice were anesthetized and the intensity of Cy5.5 fluorescence from the tumor was noninvasively quantified using FMT (FIG. 7). The tumors formed from Gli36D5 cells had approximately 4-fold more fluorescence than either tumors formed with U87-MG cells or control sham surgeries (FIG. 8A). For Gli36Δ5 and U87-MG brain tumors, these fluorescence signals corresponded to injected doses of 1.1% and 0.27%, respectively. Statistical analyses showed that the median fluorescence signals between the 2 groups were significantly different (FIG. 8A). To corroborate these data, tumors were excised and subjected to ex vivo FMT and Maestro fluorescence imaging analyses (FIGS. 8B and 8C). These measurements were in good agreement with those measurements made during the live animal imaging.

We also examined the expression of EGFRvIII in the cell lines. Western blots for the EGFRvIII on both U87-MG and Gli36D5 cells showed that the mutant receptor expression is similar for both cell lines (FIG. 6B). In addition, we examined A431 cells, a squamous carcinoma cell line, that expresses high levels of wild-type EGFR. Saturation binding studies indicated that the Kd for binding was similar to that measured with Gli36Δ5 cells. Furthermore, incubation of compound 2 with A431 cells displayed increasing fluorescence in the presence of the EGF ligand, which increases cycling of wild-type EGFR in cells.

We surmised that conjugation of the GE11 peptide via its amine resulted in lower serum stability as well as poor in vivo targeting and drug delivery due in part to the free carboxylate at the C-terminus. We aimed to develop compound 5 into a fluorescence imaging probe for noninvasive detection of tumors overexpressing EGFR and, therefore, incorporated lessons from prior studies into our probe design by conjugating the peptide via its free carboxyl-terminal end.

Example 2

Cyclic Analogues of EGF Peptide Ligands

Peptides have conformational structures based on their sequences. In the EGF peptide ligand, $Tyr^1$-$His^2$-$Trp^3$-$Tyr^4$-$Gly^5$-$Tyr^6$-$Thr^7$-$Pro^8$-$Gln^9$-$Asn^{10}$-$Val^{11}$-$Ile^{12}$ (SEQ ID NO: 1) sequence contains a turn at the Thr-Pro for binding to EGF receptors. Since linear peptides are flexible, we designed and synthesized a peptide that will stabilize that conformational turn. $Gly^5$ and $Asn^{10}$ sites were replaced with Lys and Glu, respectively, to form a side chain to side chain lactam cyclic bridge. Cy5 NIR label and miniPEG linker were also added as shown below.

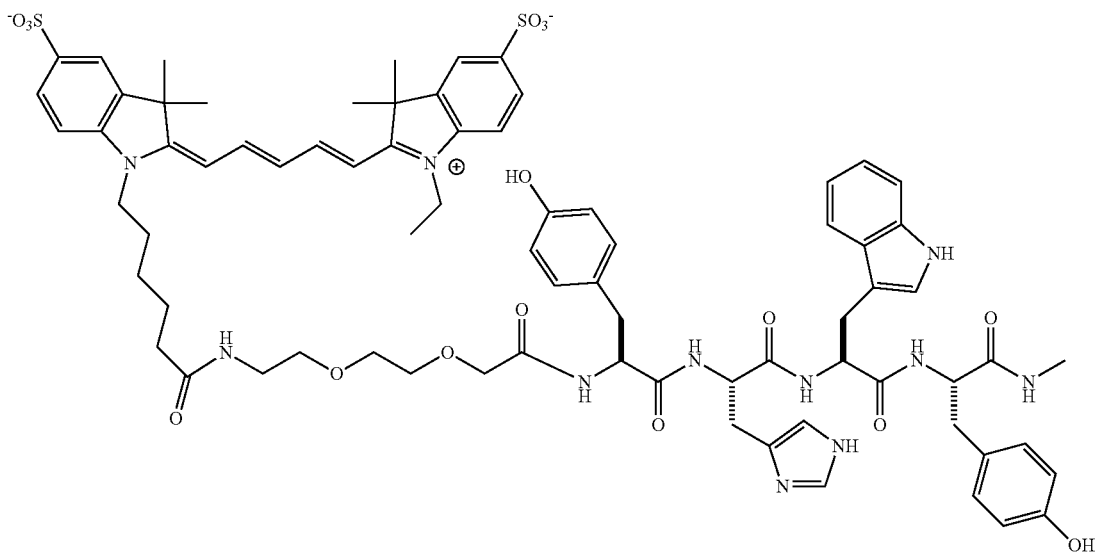

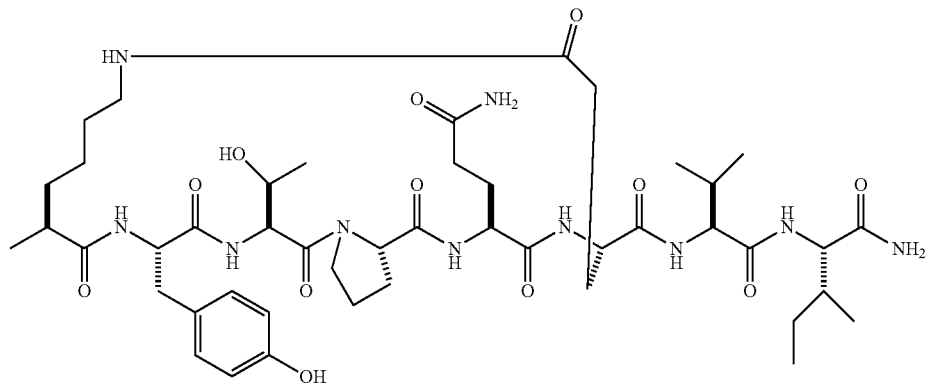

Cy5.5-miniPEG-YHWY-cyclo[KYTPQE]VI-amide.

The cyclic peptide was generated using Fmoc chemistry on solid support on a Rink amide resin. Fmoc-Glu(OAllyl)-OH and Fmoc-Lys(Alloc)-OH were used for the lactam bridge cyclization on resin. After linear sequence was coupled, the side chain groups OAllyl and Alloc were removed using palladium catalysts and the subsequent ring closure was achieved by HCTU coupling. Standard cleavage procedures were subsequently used to isolate the pure peptide. Cy5.5 conjugation was also a standard procedure.

From the above description, those skilled in the art will perceive improvements, changes and modifications. Such improvements, changes and modifications within the skill of the art are intended to be covered by the appended claims. All references, publications, and patents cited in the present application are herein incorporated by reference in their entirety.

-continued

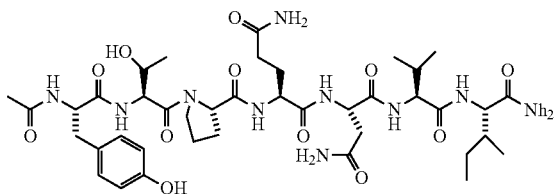

Having described the invention, we claim:

1. A method of detecting epidermal growth factor receptor (EGFR) expressing cancer cells in a subject's brain, the method comprising administering systemically to a subject a diagnostically effective amount of a probe for imaging EGFR expressing cancer cells, the probe having the following formula:

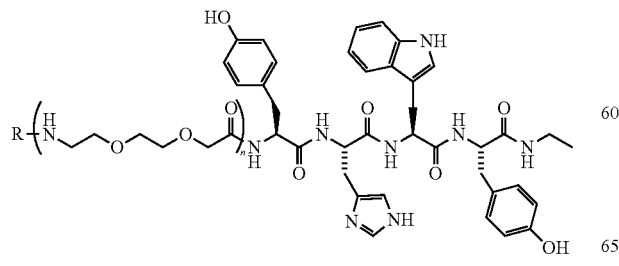

where R is a near infrared fluorescence moiety and n is an integer from 1-3; and detecting probes bound to and/or complexed with the EGFR expressing cancer cells to determine the location and/or distribution of the EGFR expressing cancer cells in the subject's brain, wherein the probe upon systemic administration to the subject is capable of crossing the subject's blood brain barrier.

2. The method of claim 1, the near infrared fluorescence moiety selected from the group consisting of Cy5.5, and ZW800-1.

3. The method of claim 1, the probe comprising the following formula:
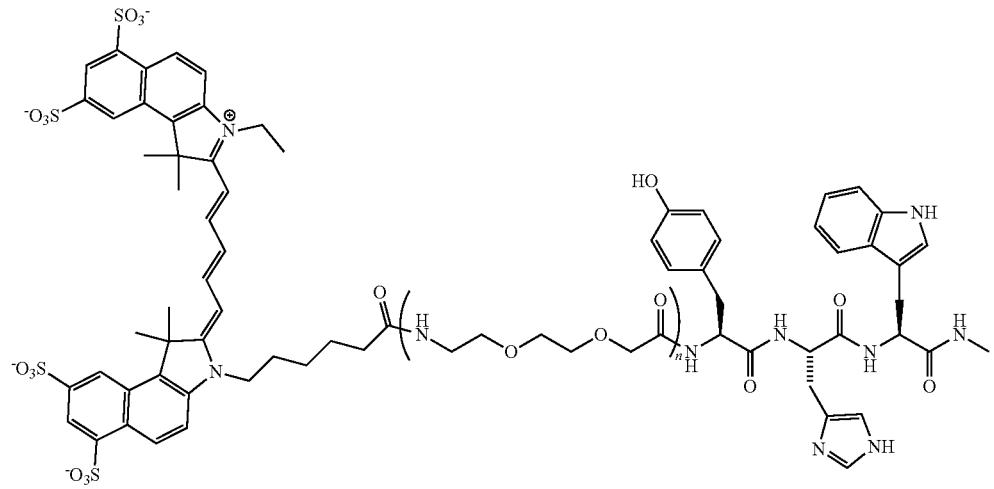
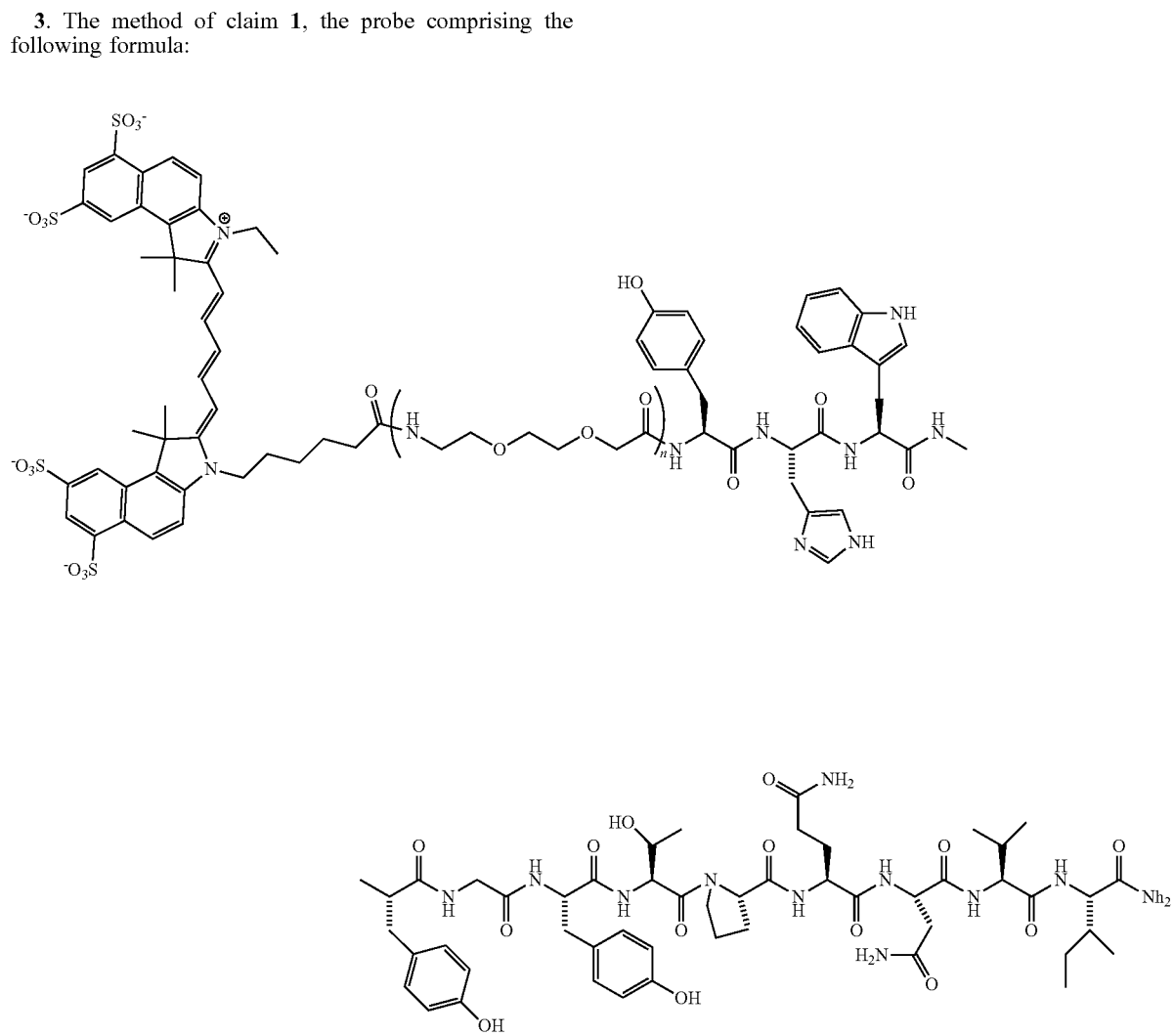
where n is an integer from 1-3.
4. The method of claim 1, the probe comprising the following formula:
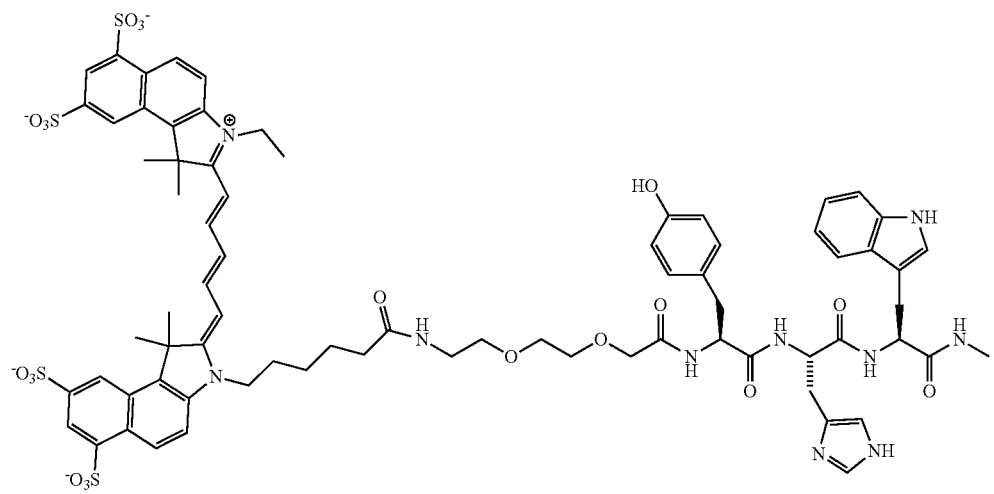

-continued
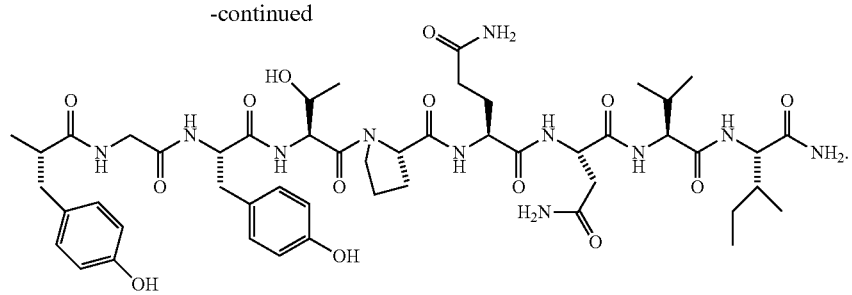
5. The method of claim 1, the EGFR expressing cancer cells comprising glioblastoma cells.
6. The method of claim 1, the EGFR expressing cancer cells being detected by Fluorescence-mediated molecular tomography (FMT).
7. The method of claim 1, the probe being detected to define a tumor margin in the subject.
* * * * *

UNITED STATES PATENT AND TRADEMARK OFFICE
CERTIFICATE OF CORRECTION

| | |
|---|---|
| PATENT NO. | : 11,708,393 B2 |
| APPLICATION NO. | : 17/224505 |
| DATED | : July 25, 2023 |
| INVENTOR(S) | : Basilion et al. |

It is certified that error appears in the above-identified patent and that said Letters Patent is hereby corrected as shown below:

In the Specification

Column 1, before the subtitle BACKGROUND insert the following paragraph:
--GOVERNMENT FUNDING
This invention was made with government support under EB012099 and CA109620 awarded by the National Institutes of Health. The government has certain rights in the invention.--

Signed and Sealed this
Thirty-first Day of October, 2023

Katherine Kelly Vidal
*Director of the United States Patent and Trademark Office*